US011969356B2

(12) United States Patent
Laurence et al.

(10) Patent No.: US 11,969,356 B2
(45) Date of Patent: Apr. 30, 2024

(54) INTERVERTEBRAL IMPLANT WITH BLADES FOR CONNECTING TO ADJACENT VERTEBRAL BODIES

(71) Applicant: DePuy Synthes Products, Inc., Raynham, MA (US)

(72) Inventors: Lawton Laurence, Phoenixville, PA (US); David T. Banks, Marlton, NJ (US); Vincent E. Mandes, Horsham, PA (US); Heather Cannon, West Chester, PA (US); Joshua McManus, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 93 days.

(21) Appl. No.: 17/498,024

(22) Filed: Oct. 11, 2021

(65) Prior Publication Data
US 2022/0023065 A1    Jan. 27, 2022

Related U.S. Application Data

(63) Continuation of application No. 16/519,553, filed on Jul. 23, 2019, now Pat. No. 11,160,667, which is a
(Continued)

(51) Int. Cl.
*A61F 2/44* (2006.01)
*A61B 17/16* (2006.01)
(Continued)

(52) U.S. Cl.
CPC ........ *A61F 2/4455* (2013.01); *A61B 17/1671* (2013.01); *A61B 17/68* (2013.01);
(Continued)

(58) Field of Classification Search
CPC ........ A61F 2/4455; A61F 2/442; A61F 2/446; A61F 2/4465; A61F 2/447
(Continued)

(56) References Cited

U.S. PATENT DOCUMENTS 6,447,546 B1  9/2002  Bramlet et al.
6,500,128 B2  12/2002  Marino
(Continued)

FOREIGN PATENT DOCUMENTS

JP  09-511659 A  11/1997
JP  2007-501040 A  1/2007
(Continued)

OTHER PUBLICATIONS

U.S. Appl. No. 16/519,553, filed Jul. 23, 2019.
(Continued)

*Primary Examiner* — Nicholas J Plionis
*Assistant Examiner* — Christina Negrellirodriguez
(74) *Attorney, Agent, or Firm* — BakerHostetler

(57) ABSTRACT

An intervertebral implant for insertion into an intervertebral disc space between adjacent vertebral bodies or between two bone portions. The implant includes a spacer portion, a plate portion operatively coupled to the spacer portion and one or more blades for securing the implant to the adjacent vertebral bodies. The blades preferably include superior and inferior cylindrical pins for engaging the adjacent vertebral bodies. The implant may be configured to be inserted via a direct lateral trans-psoas approach. Alternatively, the implant may be configured for insertion via an anterior approach.

16 Claims, 19 Drawing Sheets

Related U.S. Application Data continuation of application No. 15/637,570, filed on Jun. 29, 2017, now Pat. No. 10,369,007, which is a continuation of application No. 14/987,279, filed on Jan. 4, 2016, now Pat. No. 9,717,602, which is a continuation of application No. 13/749,972, filed on Jan. 25, 2013, now Pat. No. 9,254,198, which is a continuation of application No. 13/061,609, filed as application No. PCT/US2009/055733 on Sep. 2, 2009, now Pat. No. 8,382,843.

(60) Provisional application No. 61/093,514, filed on Sep. 2, 2008.

(51) Int. Cl.
*A61B 17/68* (2006.01)
*A61F 2/30* (2006.01)
*A61F 2/46* (2006.01)
*A61B 17/86* (2006.01)
*A61F 2/28* (2006.01)

(52) U.S. Cl.
CPC .......... *A61F 2/30767* (2013.01); *A61F 2/442* (2013.01); *A61F 2/4465* (2013.01); *A61F 2/4611* (2013.01); *A61B 17/86* (2013.01); *A61F 2/28* (2013.01); *A61F 2002/2835* (2013.01); *A61F 2002/30062* (2013.01); *A61F 2002/30131* (2013.01); *A61F 2002/30133* (2013.01); *A61F 2002/30179* (2013.01); *A61F 2002/30383* (2013.01); *A61F 2002/30507* (2013.01); *A61F 2002/30517* (2013.01); *A61F 2002/30593* (2013.01); *A61F 2002/30604* (2013.01); *A61F 2002/30607* (2013.01); *A61F 2002/30616* (2013.01); *A61F 2002/30774* (2013.01); *A61F 2002/30843* (2013.01); *A61F 2002/30845* (2013.01); *A61F 2002/30884* (2013.01); *A61F 2002/30904* (2013.01); *A61F 2002/4619* (2013.01); *A61F 2210/0004* (2013.01); *A61F 2220/0025* (2013.01); *A61F 2230/0013* (2013.01); *A61F 2230/0015* (2013.01); *A61F 2230/0058* (2013.01); *A61F 2310/00017* (2013.01); *A61F 2310/00023* (2013.01); *A61F 2310/00041* (2013.01); *A61F 2310/00047* (2013.01); *A61F 2310/00131* (2013.01); *A61F 2310/00329* (2013.01); *A61F 2310/00359* (2013.01); *A61F 2310/00407* (2013.01); *A61F 2310/00796* (2013.01)

(58) Field of Classification Search
USPC .............................. 623/17.11–17.16
See application file for complete search history.

(56) References Cited

U.S. PATENT DOCUMENTS

| | | | |
|---|---|---|---|
| 7,060,097 B2 | 6/2006 | Fraser et al. | |
| 7,079,883 B2 | 7/2006 | Marino et al. | |
| 7,177,677 B2 | 2/2007 | Kaula et al. | |
| 7,207,949 B2 | 4/2007 | Miles et al. | |
| 7,470,236 B1 | 12/2008 | Kelleher et al. | |
| 7,522,953 B2 | 4/2009 | Kaula et al. | |
| 7,582,058 B1 | 9/2009 | Miles et al. | |
| 8,027,716 B2 | 9/2011 | Gharib et al. | |
| 8,070,815 B2 | 12/2011 | Yu et al. | |
| 8,083,796 B1 | 12/2011 | Raiszadeh et al. | |
| 8,133,173 B2 | 3/2012 | Miles et al. | |
| 8,147,421 B2 | 4/2012 | Farquhar et al. | |
| 8,165,653 B2 | 4/2012 | Marino et al. | |
| 8,192,356 B2 | 6/2012 | Miles et al. | |
| 8,206,312 B2 | 6/2012 | Farquhar | |
| 8,255,045 B2 | 8/2012 | Gharib et al. | |
| 8,382,843 B2 | 2/2013 | Laurence et al. | |
| 8,617,244 B2 | 12/2013 | Reichen et al. | |
| 9,254,198 B2 | 2/2016 | Laurence et al. | |
| 9,717,602 B2 | 8/2017 | Laurence et al. | |
| 10,369,007 B2 | 8/2019 | Laurence et al. | |
| 2002/0095155 A1 | 7/2002 | Michelson | |
| 2005/0033435 A1 | 2/2005 | Belliard et al. | |
| 2005/0177245 A1 | 8/2005 | Leatherbury et al. | |
| 2005/0283239 A1 | 12/2005 | Crozet | |
| 2006/0004453 A1 | 1/2006 | Bartish et al. | |
| 2006/0085071 A1* | 4/2006 | Lechmann | A61F 2/4465 623/17.11 |
| 2006/0235533 A1* | 10/2006 | Blain | A61F 2/4455 623/17.16 |
| 2007/0239278 A1 | 10/2007 | Heinz | |
| 2009/0210062 A1 | 8/2009 | Thalgott et al. | |
| 2010/0016974 A1 | 1/2010 | Janowski et al. | |
| 2010/0312346 A1* | 12/2010 | Kueenzi | A61F 2/44 623/17.16 |
| 2011/0208311 A1 | 8/2011 | Janowski | |
| 2011/0230971 A1* | 9/2011 | Donner | A61F 2/4455 606/246 |
| 2012/0078371 A1 | 3/2012 | Gamache et al. | |
| 2012/0253406 A1 | 10/2012 | Bae et al. | |

FOREIGN PATENT DOCUMENTS

| | | |
|---|---|---|
| JP | 2007-521885 A | 8/2007 |
| JP | 2008-504870 A | 2/2008 |
| WO | 95/26164 A1 | 10/1995 |
| WO | 2005/077039 A2 | 8/2005 |
| WO | 2009/064644 A1 | 5/2009 |
| WO | 2009/132110 A1 | 10/2009 |

OTHER PUBLICATIONS

U.S. Appl. No. 15/637,570, filed Jun. 29, 2017.
U.S. Appl. No. 14/987,279, filed Jan. 4, 2016.
U.S. Appl. No. 13/749,972, filed Jan. 25, 2013.
U.S. Appl. No. 13/061,609, filed Mar. 1, 2011.
International Patent Application No. PCT/US2009/055733: International Search Report and Written Opinion dated Feb. 19, 2010, 20 pages.

* cited by examiner

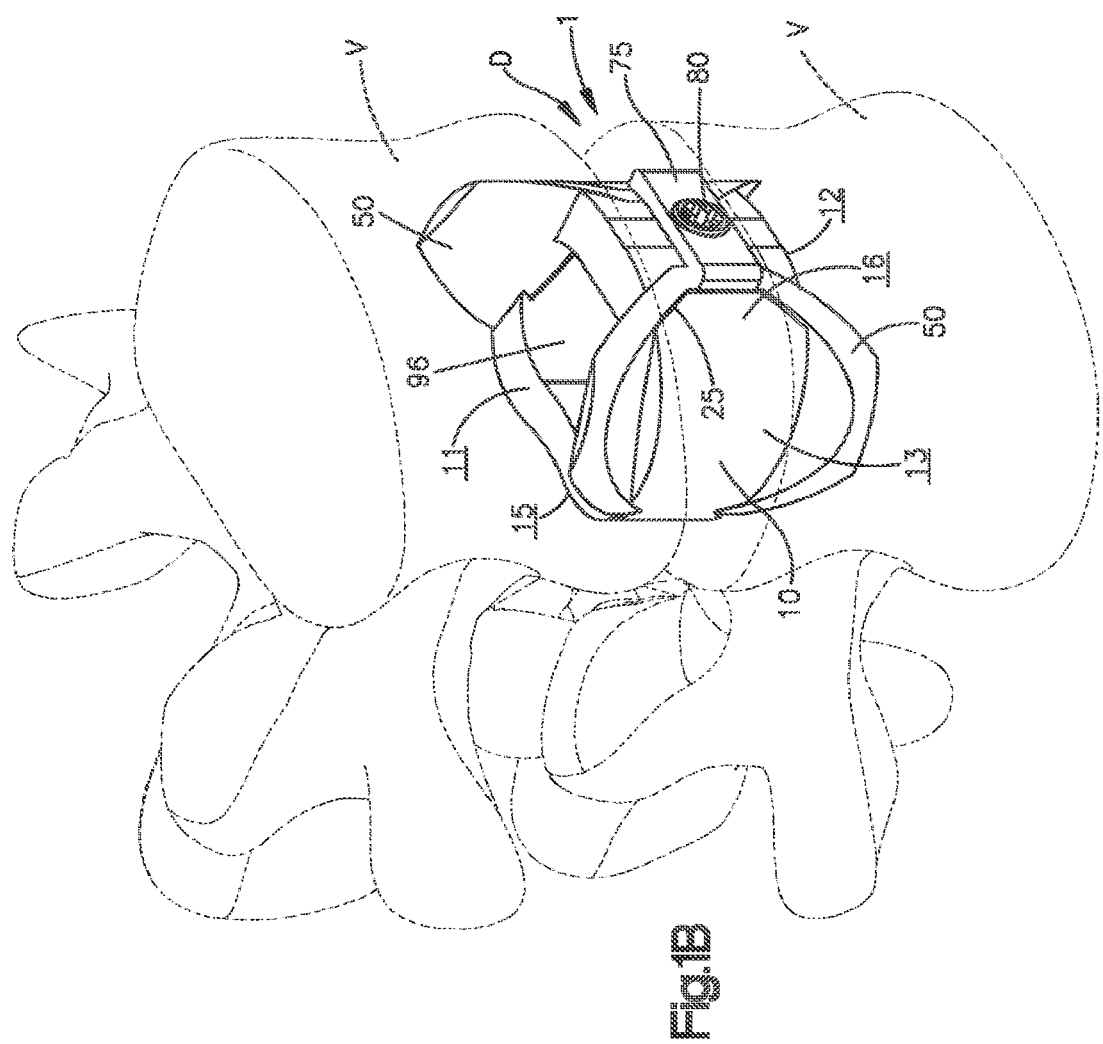

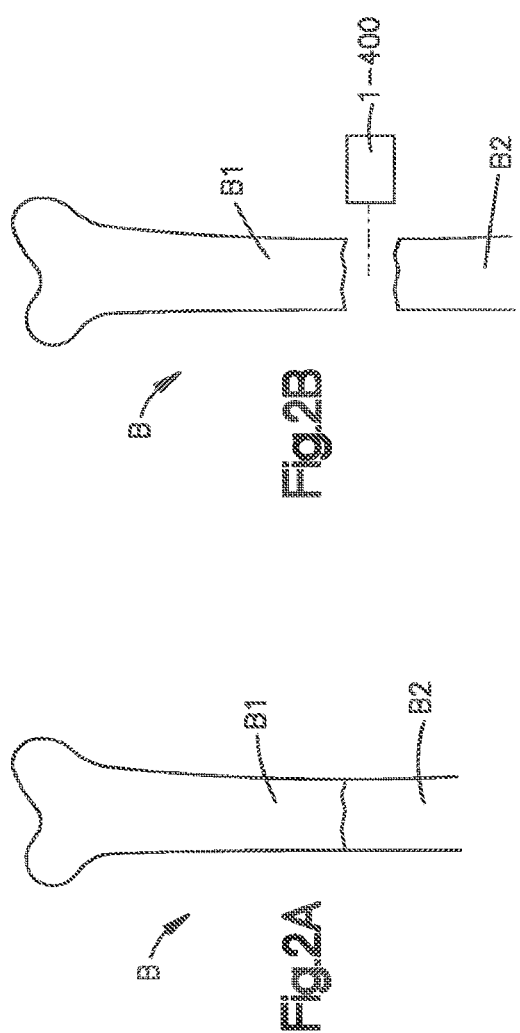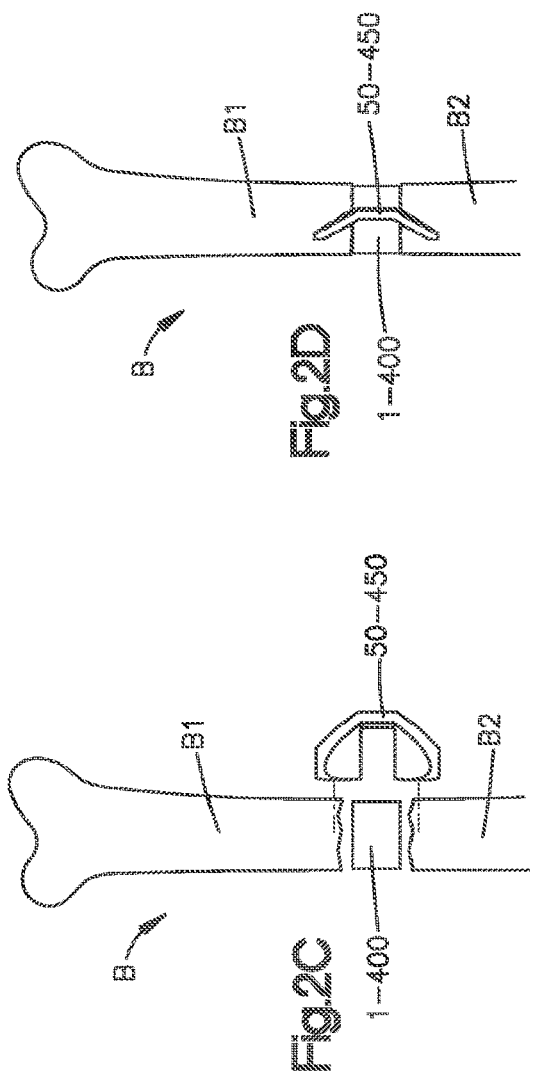

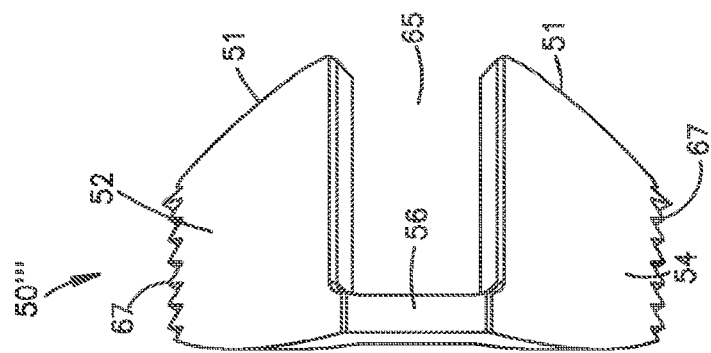
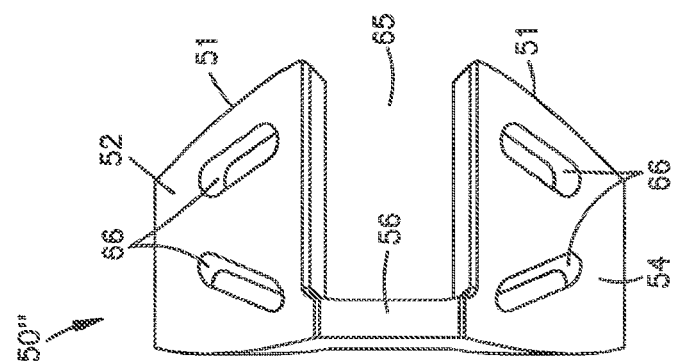
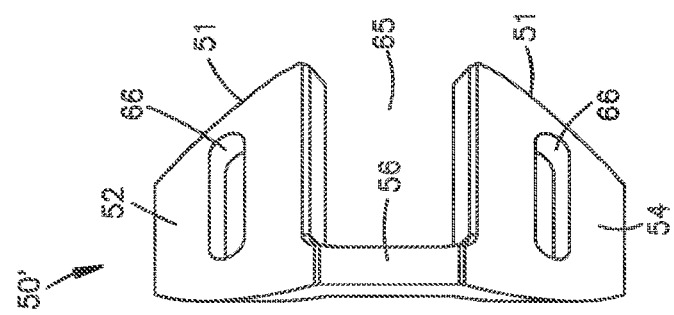
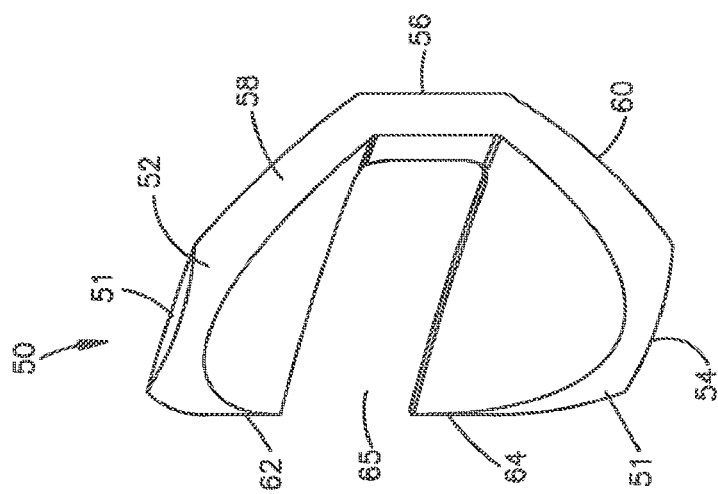

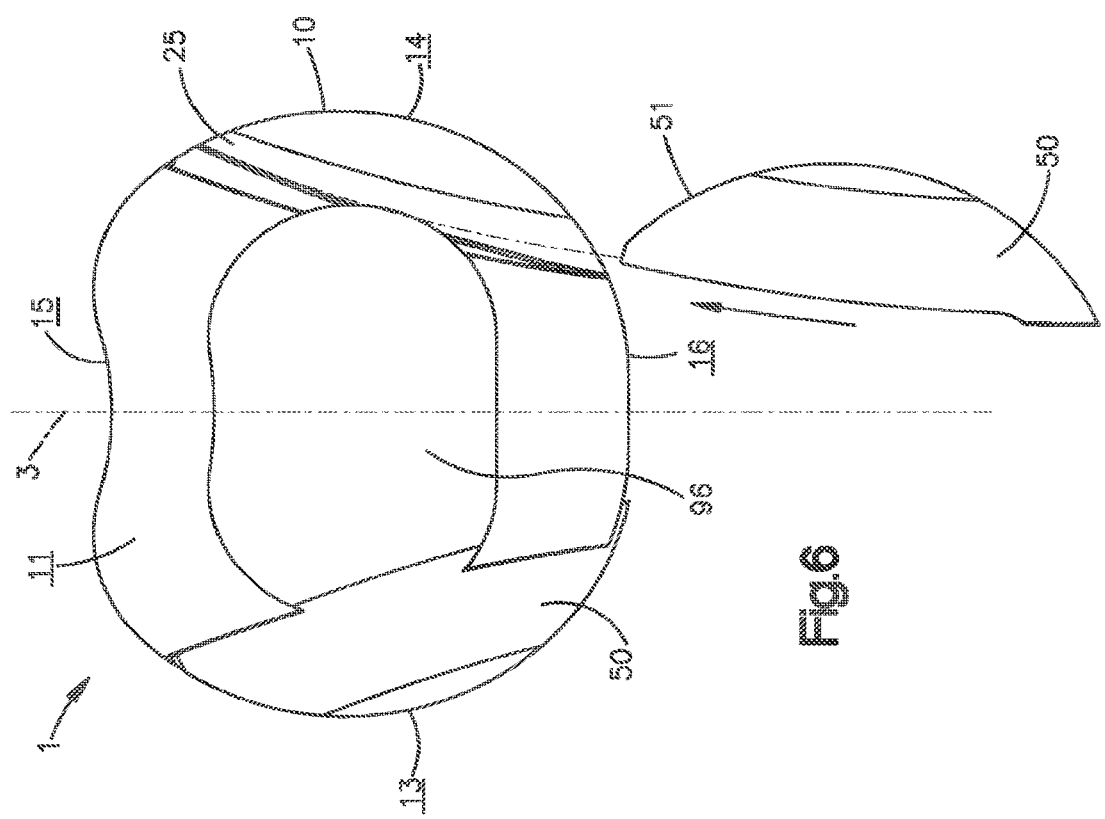

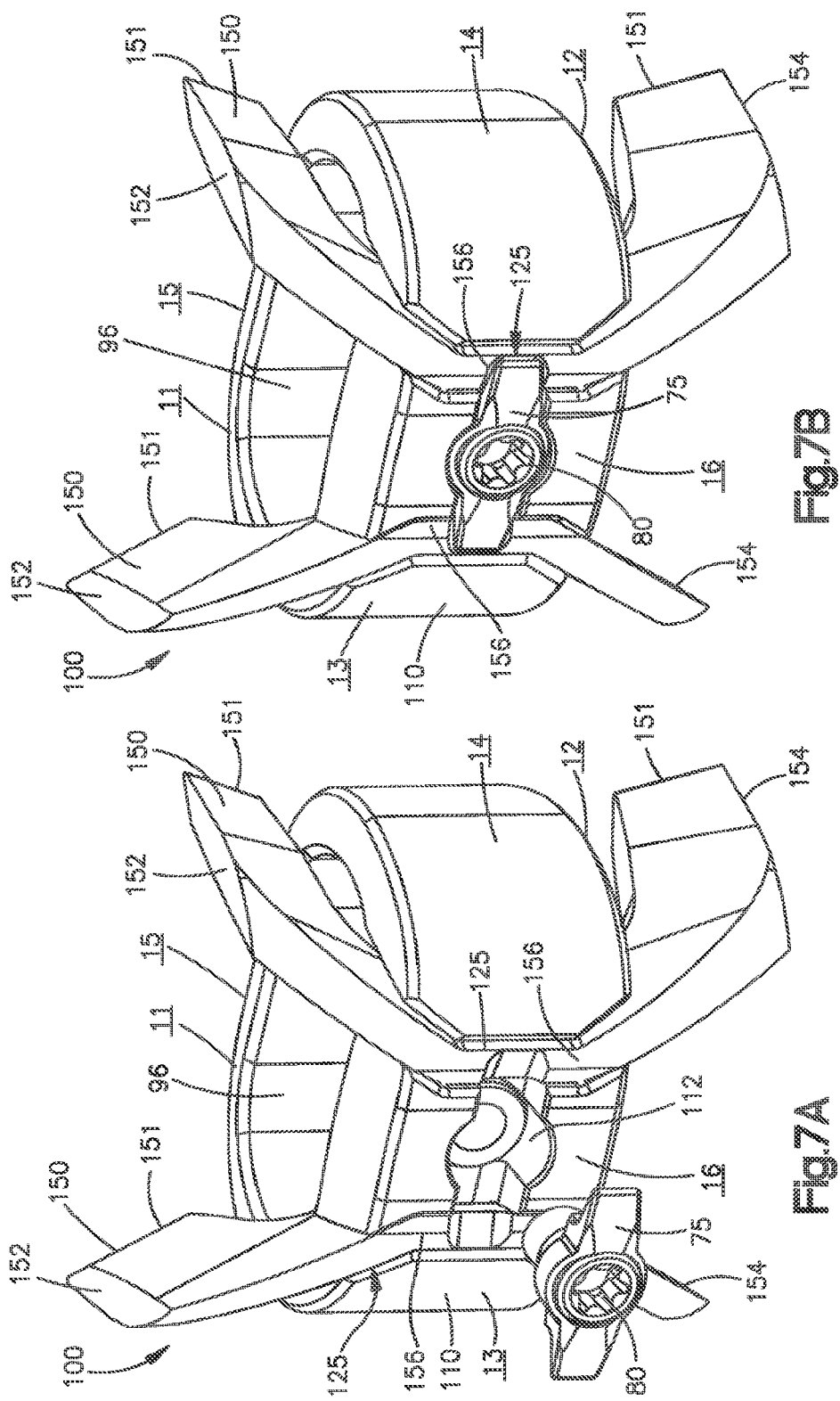

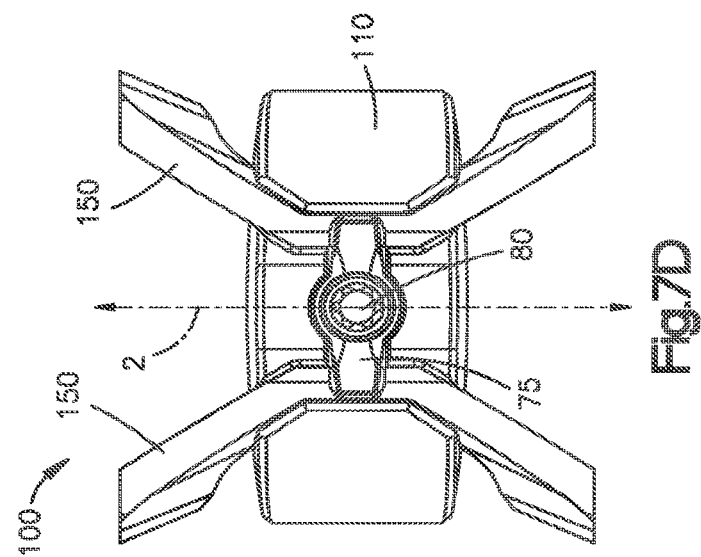
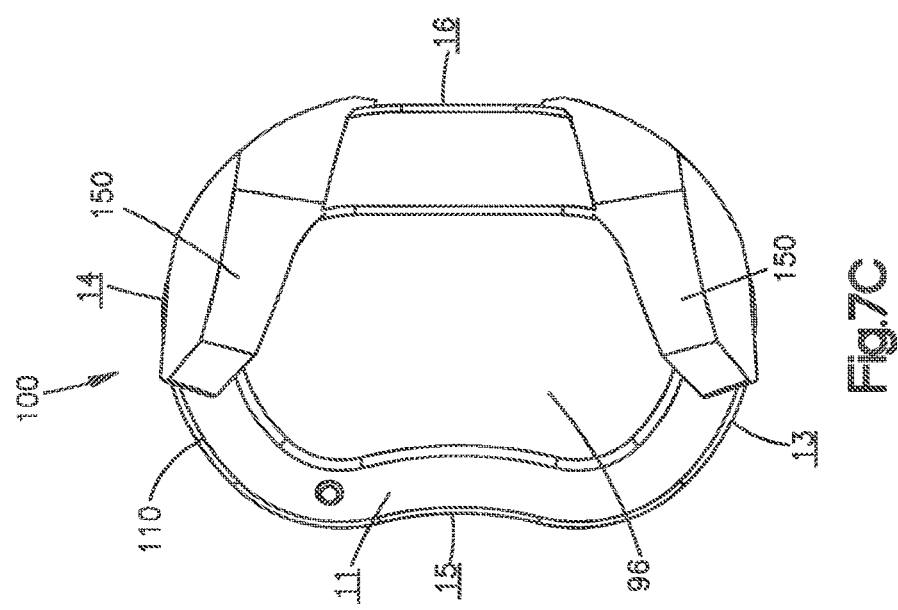

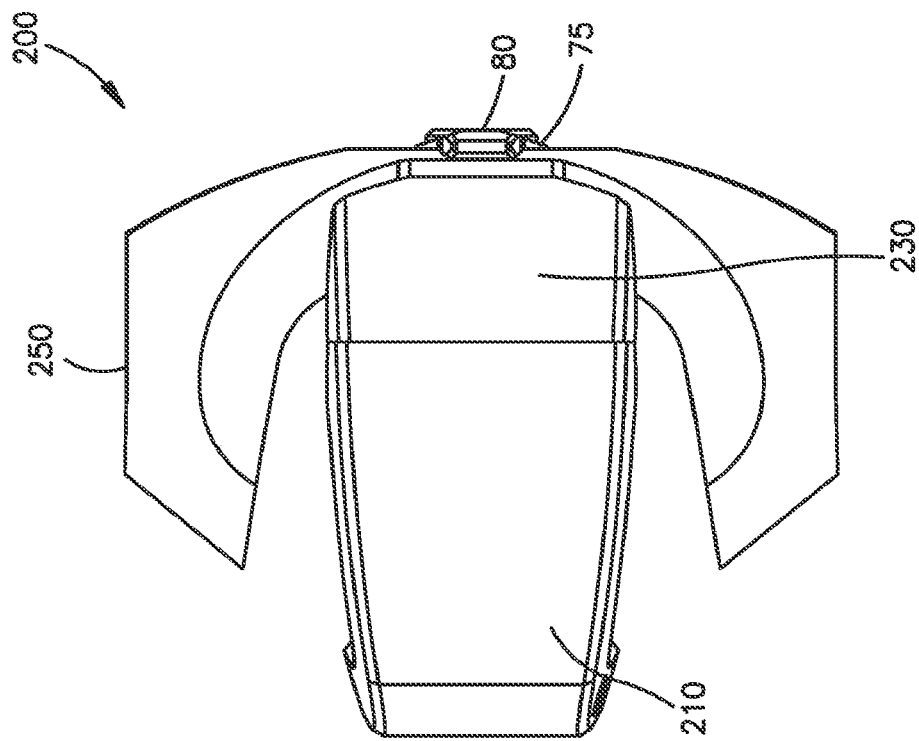
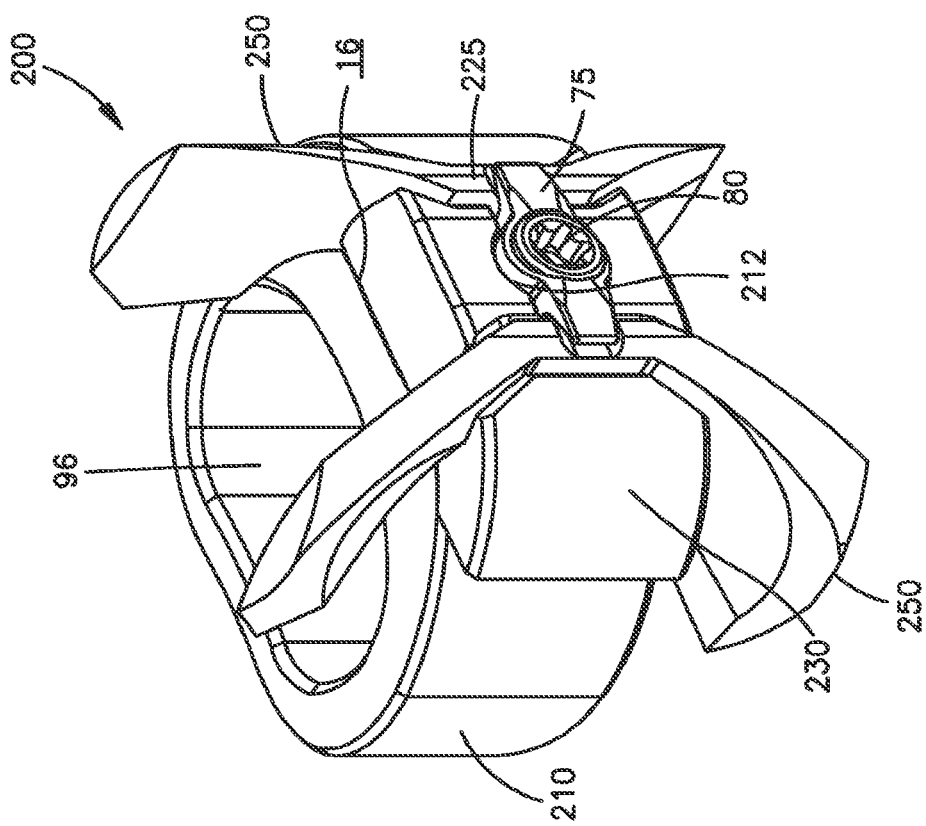

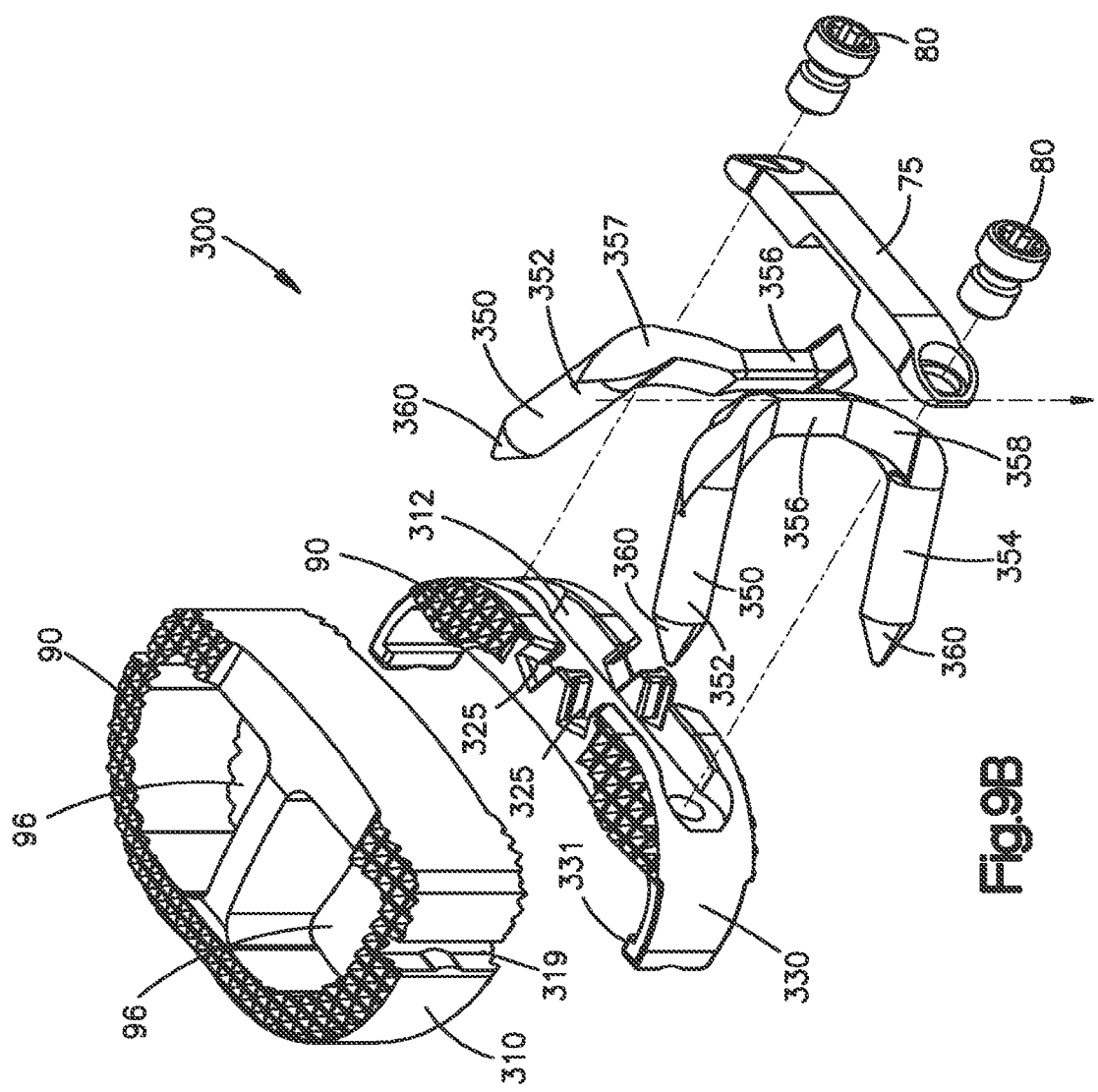
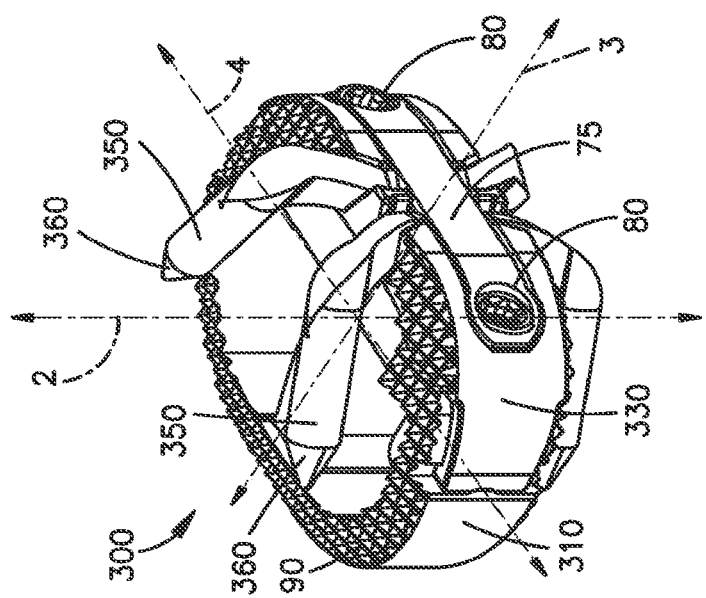
Fig.9B
Fig.9A

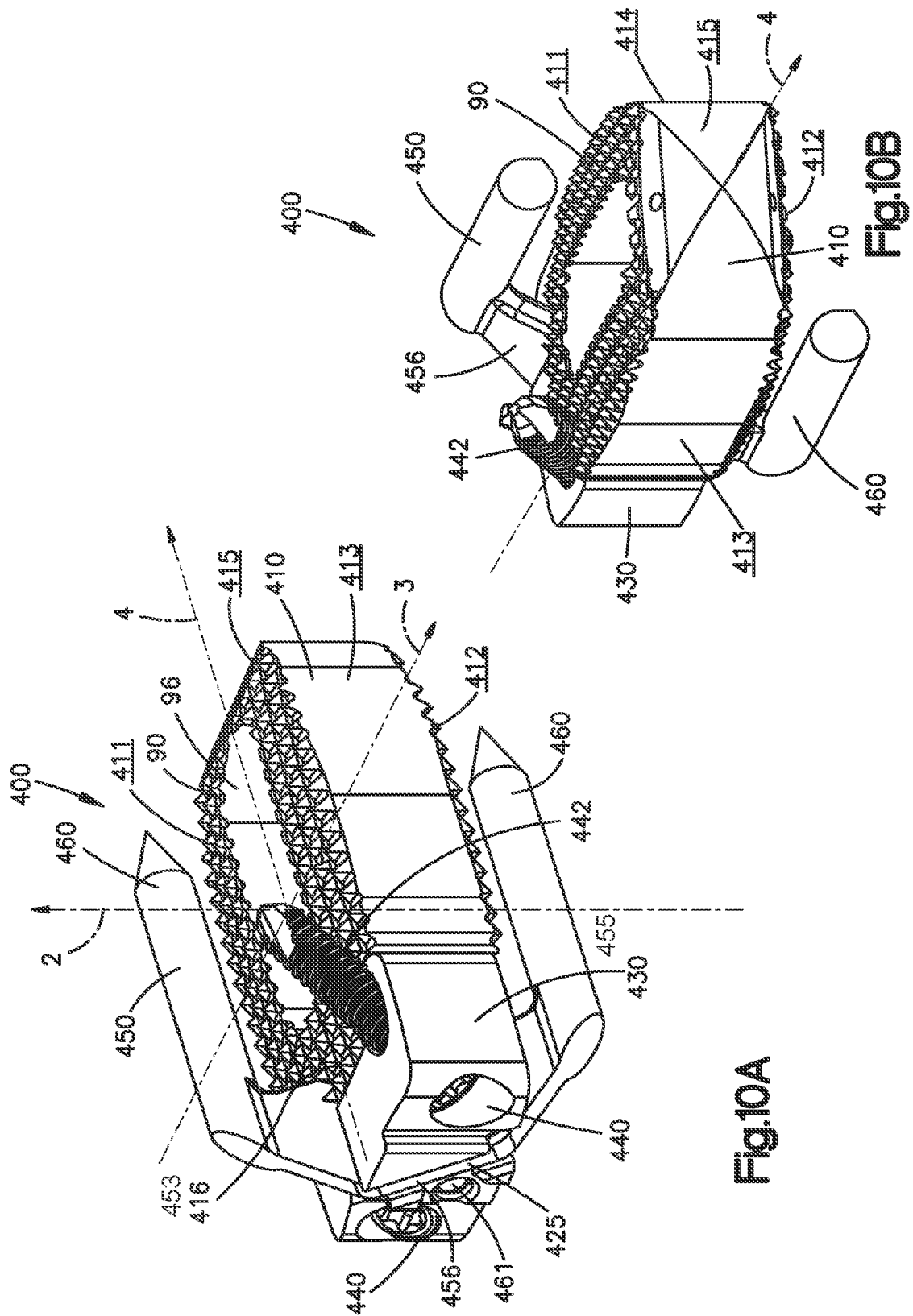

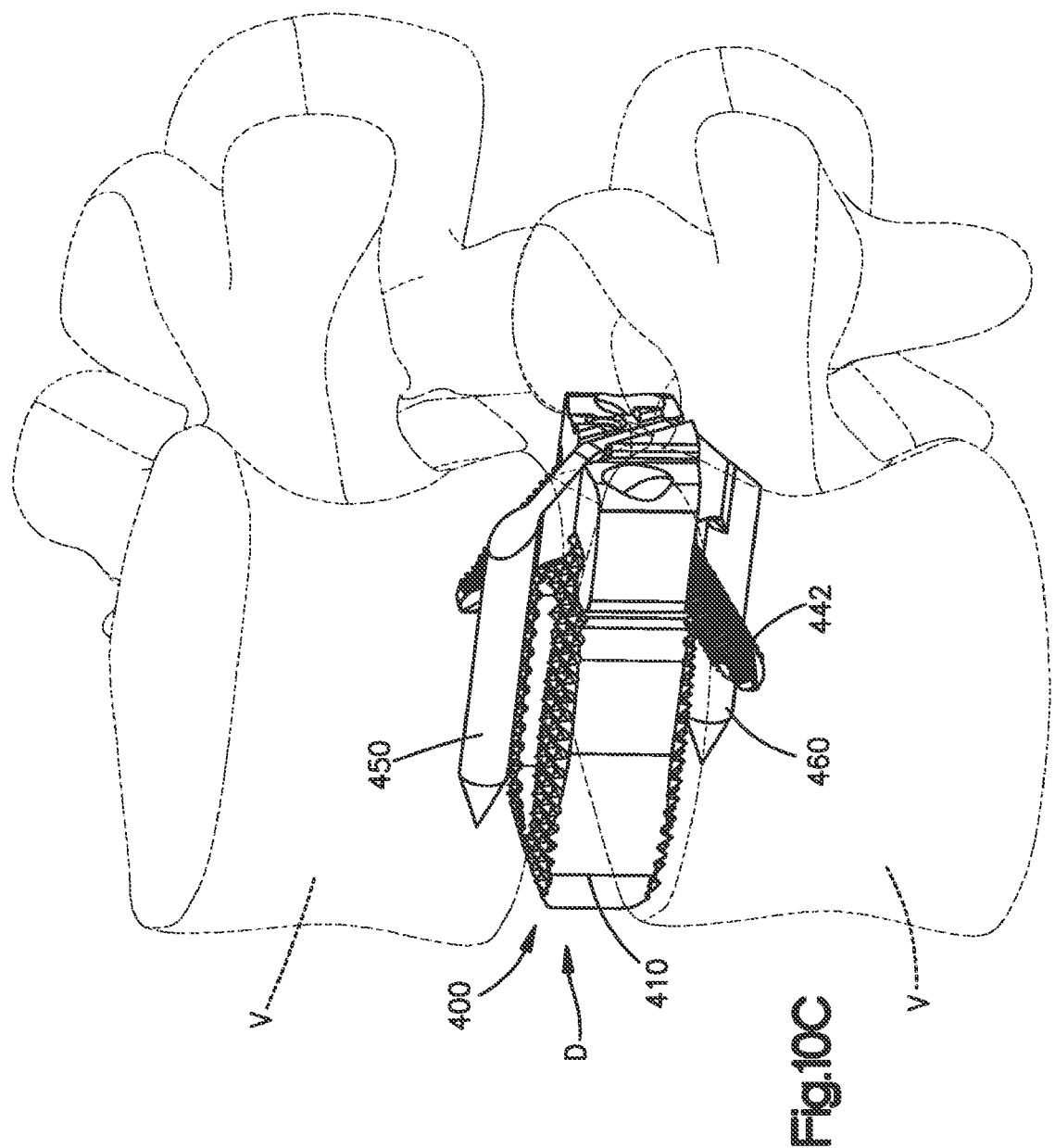

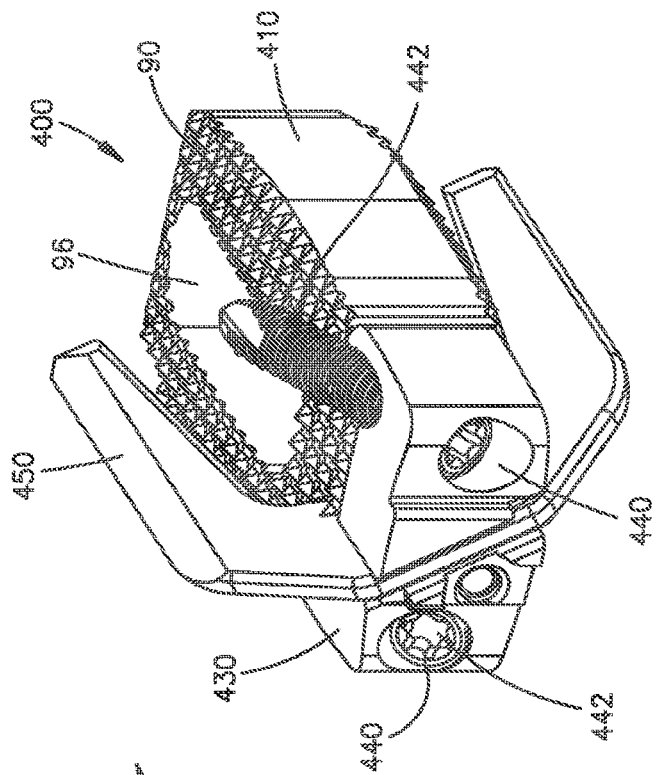
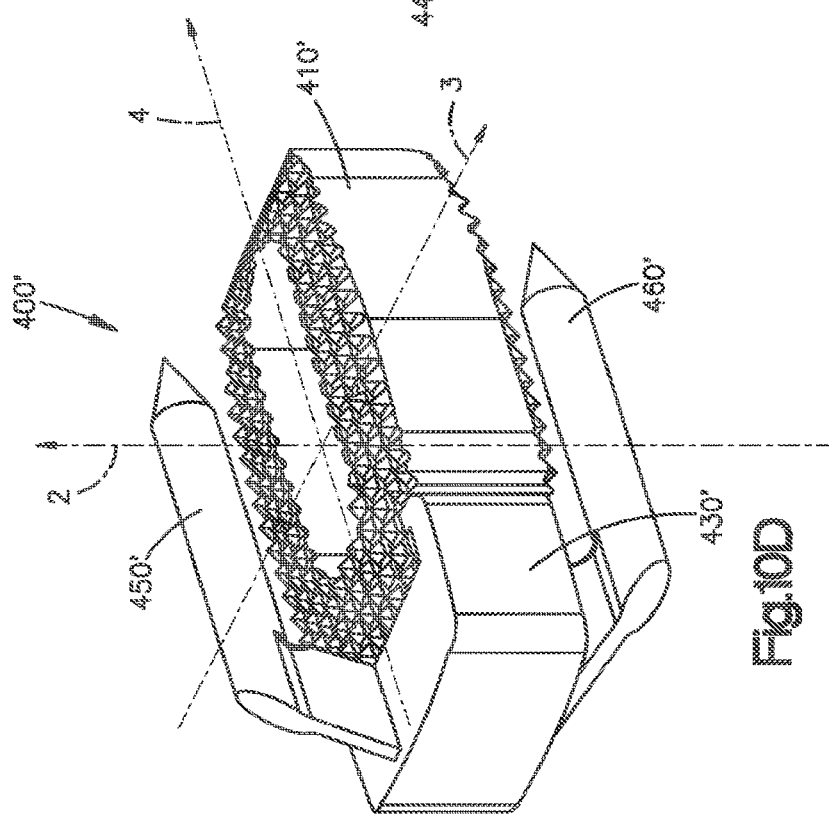

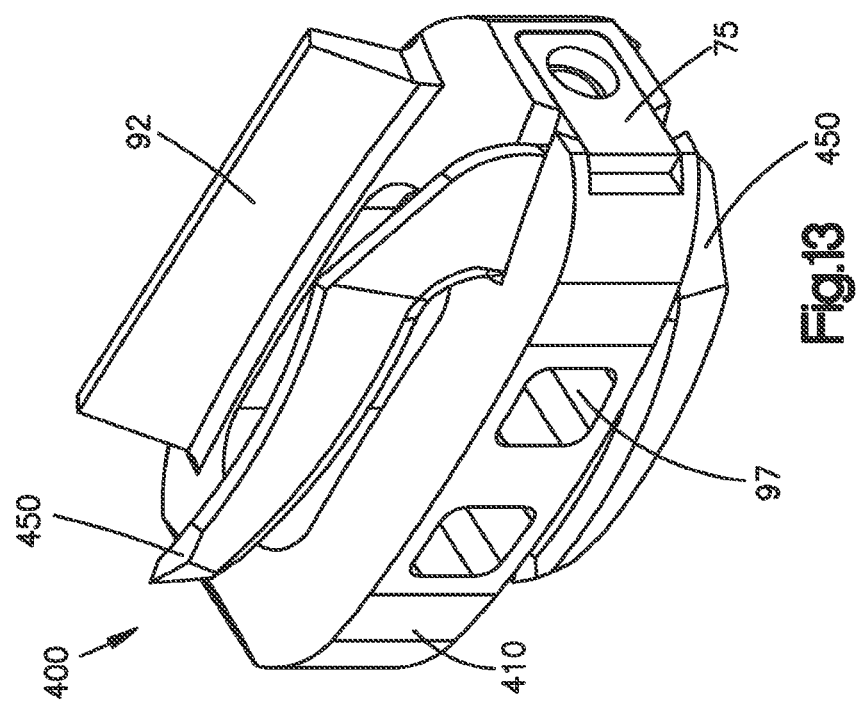
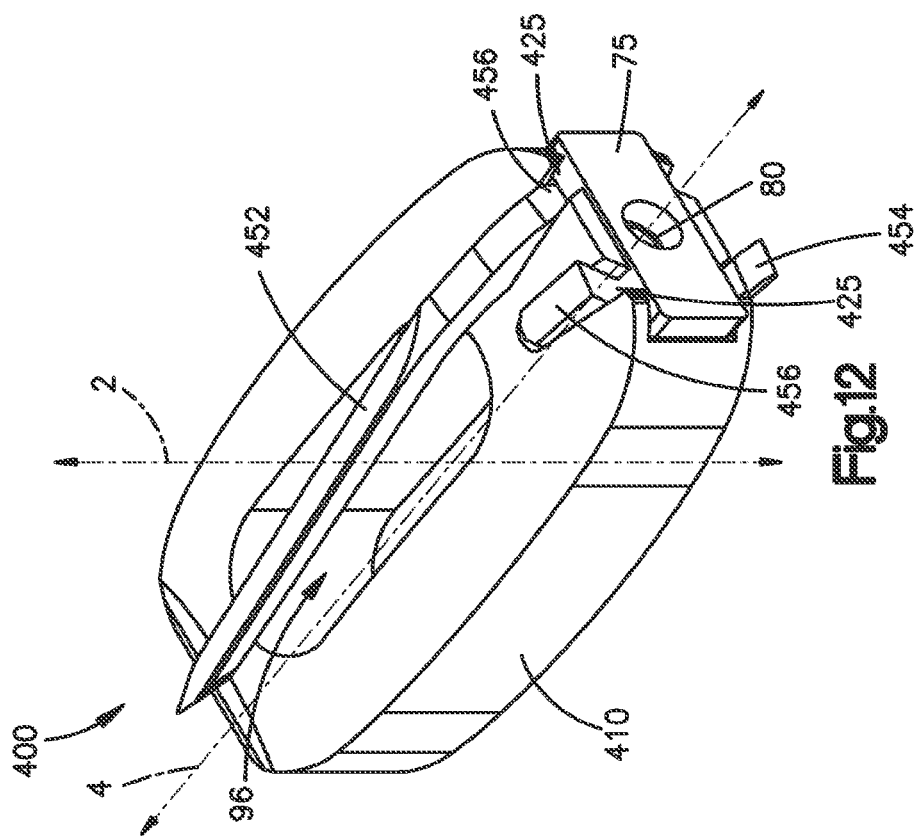

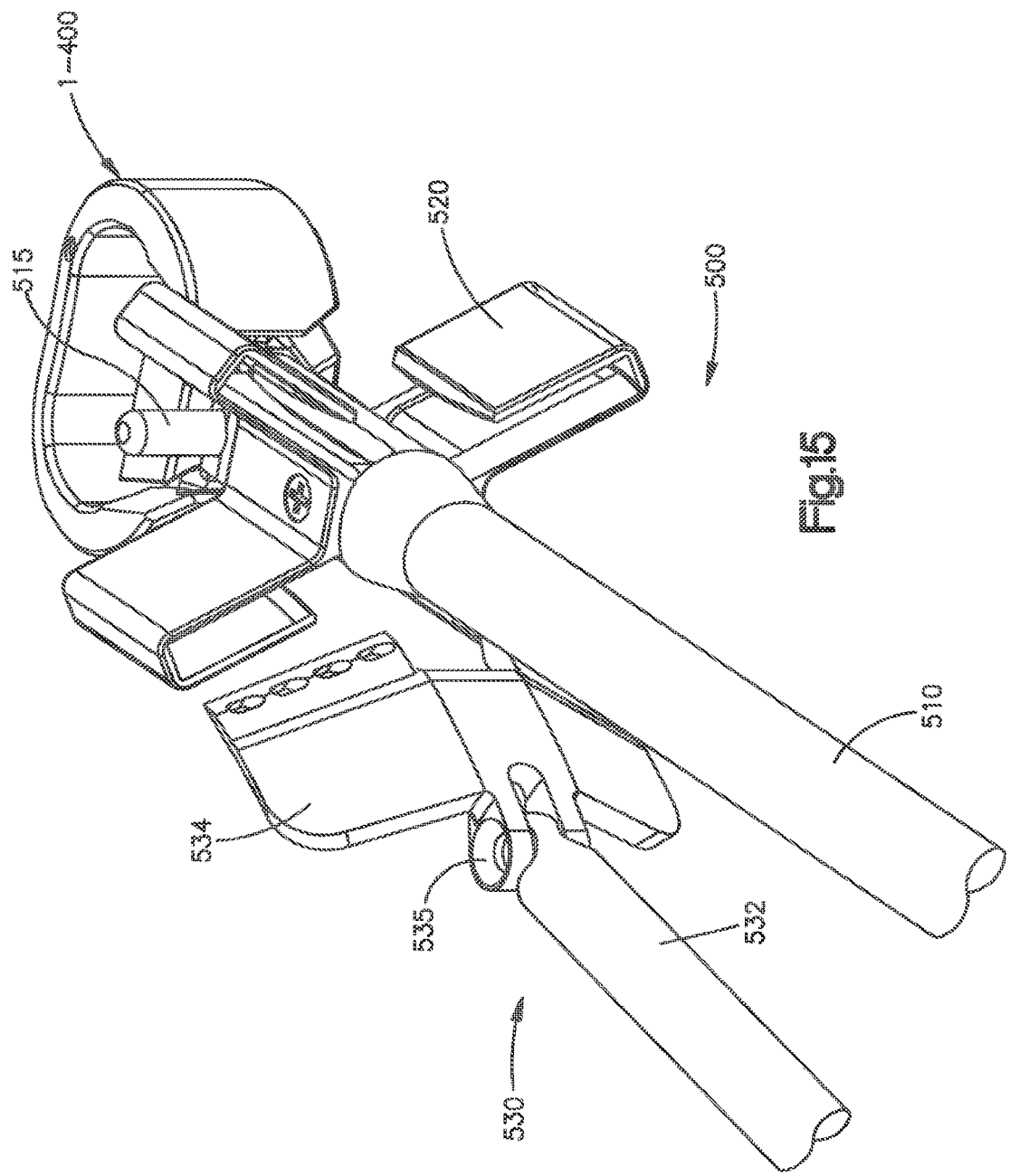

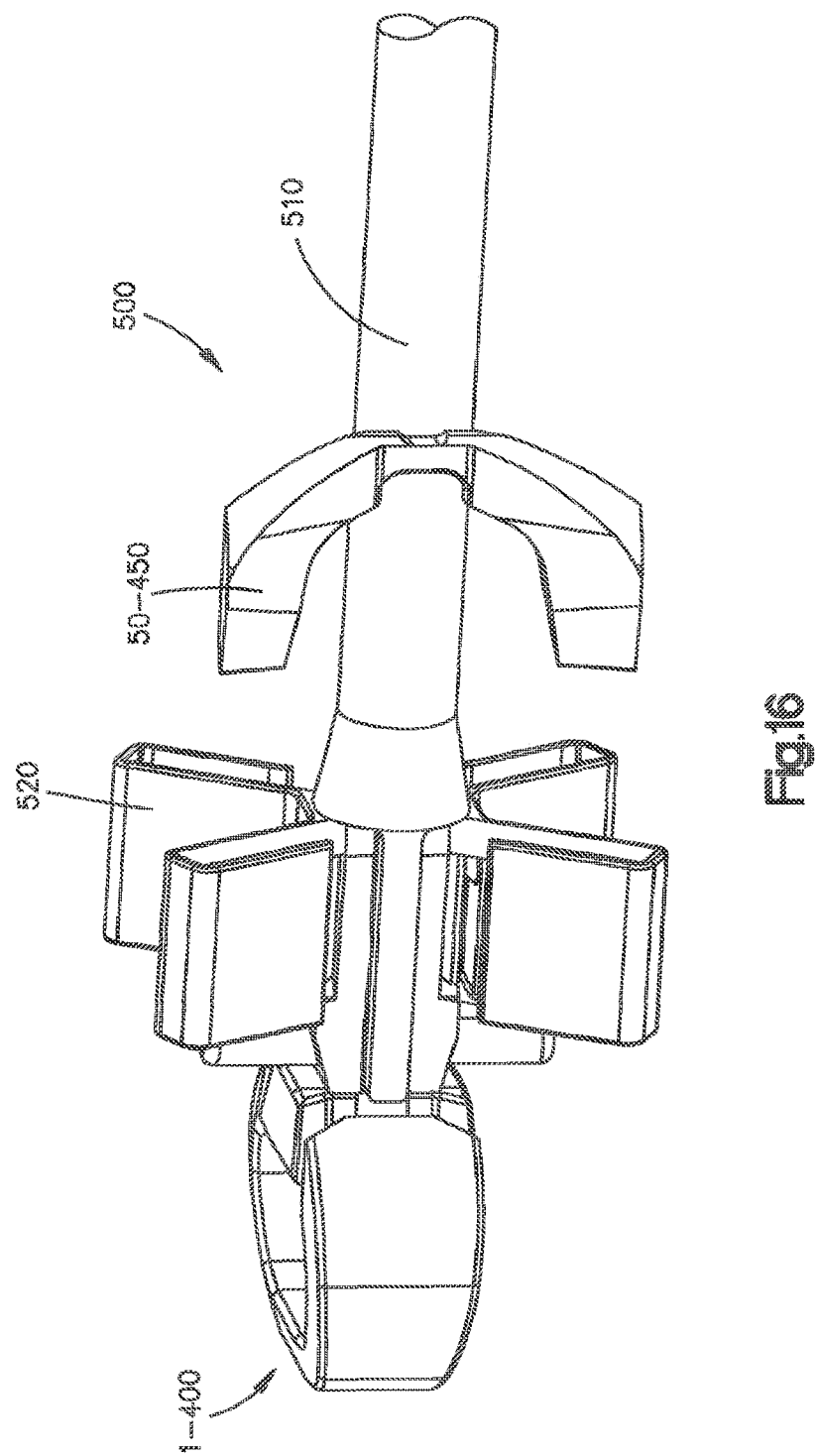

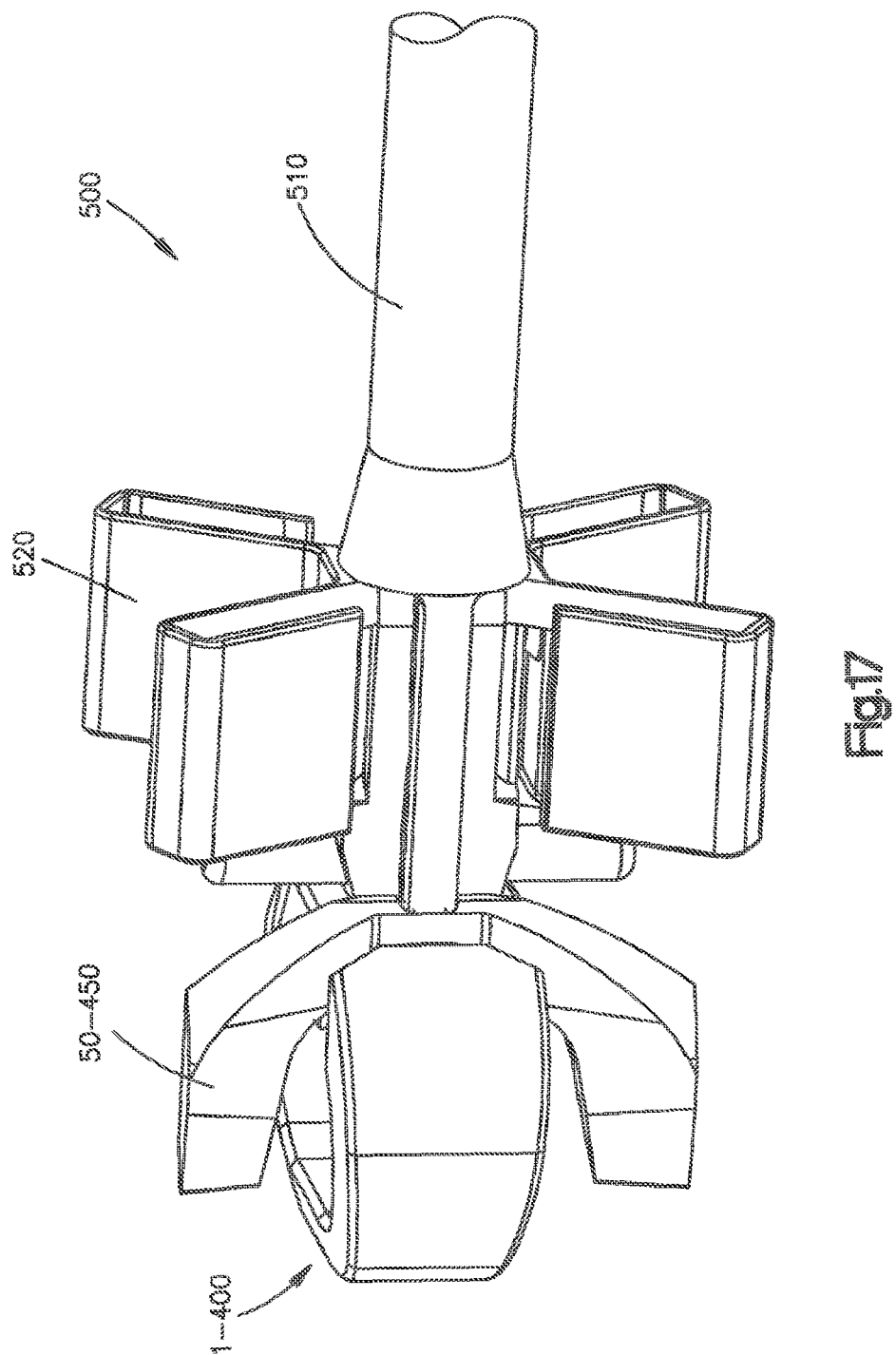

INTERVERTEBRAL IMPLANT WITH BLADES FOR CONNECTING TO ADJACENT VERTEBRAL BODIES

CROSS-REFERENCE TO RELATED APPLICATIONS

This application is a continuation of U.S. patent application Ser. No. 16/519,553 filed Jul. 23, 2019, which is a continuation of U.S. patent application Ser. No. 15/637,570 filed Jun. 29, 2017, which is a continuation of U.S. patent application Ser. No. 14/987,279 filed Jan. 4, 2016, which is a continuation of U.S. patent application Ser. No. 13/749,972 filed Jan. 25, 2013, now U.S. Pat. No. 9,254,198 issued Feb. 9, 2016, which is a continuation of U.S. patent application Ser. No. 13/061,609, filed Mar. 1, 2011, now U.S. Pat. No. 8,382,843 issued Feb. 26, 2013, which is the National Stage of International Application No. PCT/US2009/055733, filed Sep. 2, 2009, which claims the benefit of U.S. Provisional Patent Application No. 61/093,514, filed Sep. 2, 2008, the disclosures of which are incorporated herein by reference in their entireties for all purposes.

BACKGROUND OF THE INVENTION

Millions of people suffer from back pain. In some instances, in order to relieve back pain and/or to stabilize the spinal structure, adjacent vertebral bodies of a patient's spine are fused. One known method for fusing adjacent vertebral bodies is to implant one or more intervertebral implants into the affected disc space. Surgeons may stabilize the inserted intervertebral implant by securing it to the adjacent vertebral bodies with a plurality of bone screws. However, each of the bone screws is typically fastened at a different angle, which can create a situation of suboptimal surgical exposure.

It would be preferable to develop a stand-alone fusion intervertebral implant that eliminates the use of bone screws, limits surgical exposure and maintains a relatively rigid final construction.

BRIEF SUMMARY OF THE INVENTION

The present invention relates generally to an implant. More specifically, the present invention relates to an intervertebral implant for implantation into an intervertebral disc space between adjacent vertebral bodies.

The preferred implant of the present application includes a spacer portion and one or more blade elements for securing the implant to the adjacent vertebral bodies. The implant may also include a plate portion operatively coupled to the spacer portion. The blades preferably include superior and inferior cylindrical pins for engaging the adjacent vertebral bodies.

In one exemplary embodiment, the intervertebral implant includes an interbody spacer portion, a plate portion and first and second blade elements. The spacer portion includes a top surface for contacting a first vertebral body, a bottom surface for contacting a second vertebral body, a first side surface, a second side surface, a leading surface, and a trailing surface. The plate portion is operatively coupled to the interbody spacer portion and includes a top surface, a bottom surface, a first side surface, a second side surface and a trailing surface. The plate portion further includes first and second blade receiving channels extending from the trailing surface thereof. The first and second blade elements each include a first cylindrical pin for engaging the first vertebral body, a second cylindrical pin for engaging the second vertebra, and an intermediate portion for operatively coupling the first and second cylindrical pins. The intermediate portion is preferably insertable into one of the first and second blade receiving channels extending from the trailing surface of the plate portion.

In another exemplary embodiment, the intervertebral implant includes an interbody spacer portion, a plate portion and at least one blade element. The spacer portion includes a top surface for contacting a first vertebral body, a bottom surface for contacting a second vertebral body, a first side surface, a second side surface, a leading surface, and a trailing surface. The first and second side surfaces each have a length that is longer than a length of each of the leading and trailing surfaces so that, upon implantation, the implant has a medial-lateral width that is longer than its anterior-posterior depth. The plate portion includes a top surface, a bottom surface, a first side surface, a second side surface, a leading surface for operatively contacting the trailing surface of the interbody spacer portion and a trailing surface. The plate portion further includes at least one blade receiving channel extending from the trailing surface. The blade element includes a first cylindrical pin for engaging the first vertebral body, a second cylindrical pin for engaging the second vertebra, and an intermediate portion for operatively coupling the first and second cylindrical pins. The intermediate portion is preferably insertable into the blade receiving channel formed in the plate portion. The intervertebral implant is preferably adapted as a stand alone, laterally insertable implant for insertion using a direct lateral transpsoas approach without supplemental rigid fixation.

The cylindrical pins are preferably adapted to be received in a predrilled borehole formed in the adjacent vertebral bodies. The blade elements are each preferably integrally formed.

The intervertebral implant may further include a blocking element at least partially received in a recess formed in the plate portion and for overlapping at least a portion of the blade elements after the blade elements have been inserted into the blade receiving channels. The blocking element is preferably coupled to the plate portion by at least one fastener.

In another exemplary embodiment, the intervertebral implant preferably includes an interbody spacer portion, a plate portion and at least one blade element. The blade element(s) is integrally formed with the plate portion.

The present invention is also directed to an exemplary method for inserting an intervertebral implant into a disc space. The method preferably includes the steps of coupling the implant to an insertion and guide instrument, forming an incision in the patient's skin and a passageway to the disc space, inserting the implant into the disc space through the passageway with the insertion and guide instrument, drilling a first borehole into the first vertebral body and a second borehole into the second vertebral body using a drill guided by the insertion and guide instrument, inserting the blade element into the blade receiving channel formed in a trailing surface of the plate portion, inserting a first cylindrical pin associated with the blade element into the first borehole and a second cylindrical pin associated with the blade element into the second borehole and closing the incision.

In one preferred embodiment, the passageway for inserting the intervertebral implant is via a direct lateral transpsoas approach and the incision is closed without providing any additional supplemental rigid fixation to secure the implant to the adjacent vertebral bodies.

BRIEF DESCRIPTION OF THE SEVERAL VIEWS OF THE DRAWINGS

The foregoing summary, as well as the following detailed description of the preferred embodiments of the application, will be better understood when read in conjunction with the appended drawings. For the purposes of illustrating preferred embodiments of the intervertebral implant and associated method of use of the present invention, drawings of the preferred embodiments are shown. It should be understood, however, that the application is not limited to the precise arrangement, structures, features, embodiments, aspects, and instrumentalities shown, and that the arrangements, structures, features, embodiments, aspects and instrumentalities shown may be used singularly or in combination with other arrangements, structures, features, aspects, embodiments and instrumentalities. In the drawings:

FIG. 1B illustrates a top perspective view of the intervertebral implant of FIG. 1A, the intervertebral implant inserted into an intervertebral disc space between adjacent vertebral bodies;

FIG. 2A-2D illustrate various views of a method of inserting an implant according to the present invention into a fractured space of a long bone;

FIG. 5A illustrates a side perspective view of a blade element of the intervertebral implant shown in FIG. 1A;

FIG. 5B illustrates a side elevational view of a blade element according to a second preferred embodiment, which may be utilized with the implant of FIG. 1A;

FIG. 5C illustrates a side elevational view of a blade element according to a third preferred embodiment, which may be utilized with the implant of FIG. 1A;

FIG. 5D illustrates a side elevational view of a blade element according to a fourth preferred embodiment, which may be utilized with the implant of FIG. 1A;

FIG. 6 illustrates an exploded, top plan view of the intervertebral implant shown in FIG. 1A with the blade element being inserted into the spacer portion;

FIG. 7A illustrates a partially exploded, side perspective view of an intervertebral implant according to a second preferred embodiment of the present application;

FIG. 7B illustrates an alternate, side perspective view of the intervertebral implant shown in FIG. 7A;

FIG. 7C illustrates a top plan view of the intervertebral implant shown in FIG. 7A;

FIG. 7D illustrates an anterior elevational view of the intervertebral implant shown in FIG. 7A;

FIG. 8A illustrates a top perspective view of an intervertebral implant according to a third preferred embodiment of the present application;

FIG. 8B illustrates a side elevational view of the intervertebral implant shown in FIG. 8A;

FIG. 9A illustrates a top perspective view of an intervertebral implant according to a fourth preferred embodiment of the present application;

FIG. 9B illustrates an exploded, top perspective view of the intervertebral implant shown in FIG. 9A;

FIG. 10A illustrates a side perspective view of an intervertebral implant according to a fifth preferred embodiment of the present application;

FIG. 10B illustrates a front perspective view of the intervertebral implant shown in FIG. 10A;

FIG. 10C illustrates a side perspective view of the intervertebral implant shown in FIG. 10A, the intervertebral implant inserted into an intervertebral disc space between adjacent vertebral bodies;

FIG. 10D illustrates a side perspective view of an alternate exemplary embodiment of the intervertebral implant shown in FIG. 10A, wherein the plate portion and the blade elements are integrally formed;

FIG. 11 illustrates a rear perspective view of the intervertebral implant shown in FIG. 10A incorporating alternate exemplary blade elements;

FIG. 12 illustrates a top perspective view of the intervertebral implant shown in FIG. 11 incorporating separate superior and inferior blade receiving channels;

FIG. 13 illustrates a top perspective view of the intervertebral implant shown in FIG. 11 incorporating an integrated keel extending from the top and bottom surfaces thereof; and FIGS. 14-17 illustrate various views of an exemplary method for inserting an intervertebral implant according to the present invention into an intervertebral disc space between adjacent vertebral bodies, the intervertebral implant being coupled to an exemplary insertion and guide instrument.

DETAILED DESCRIPTION OF THE INVENTION

Figure 1A:
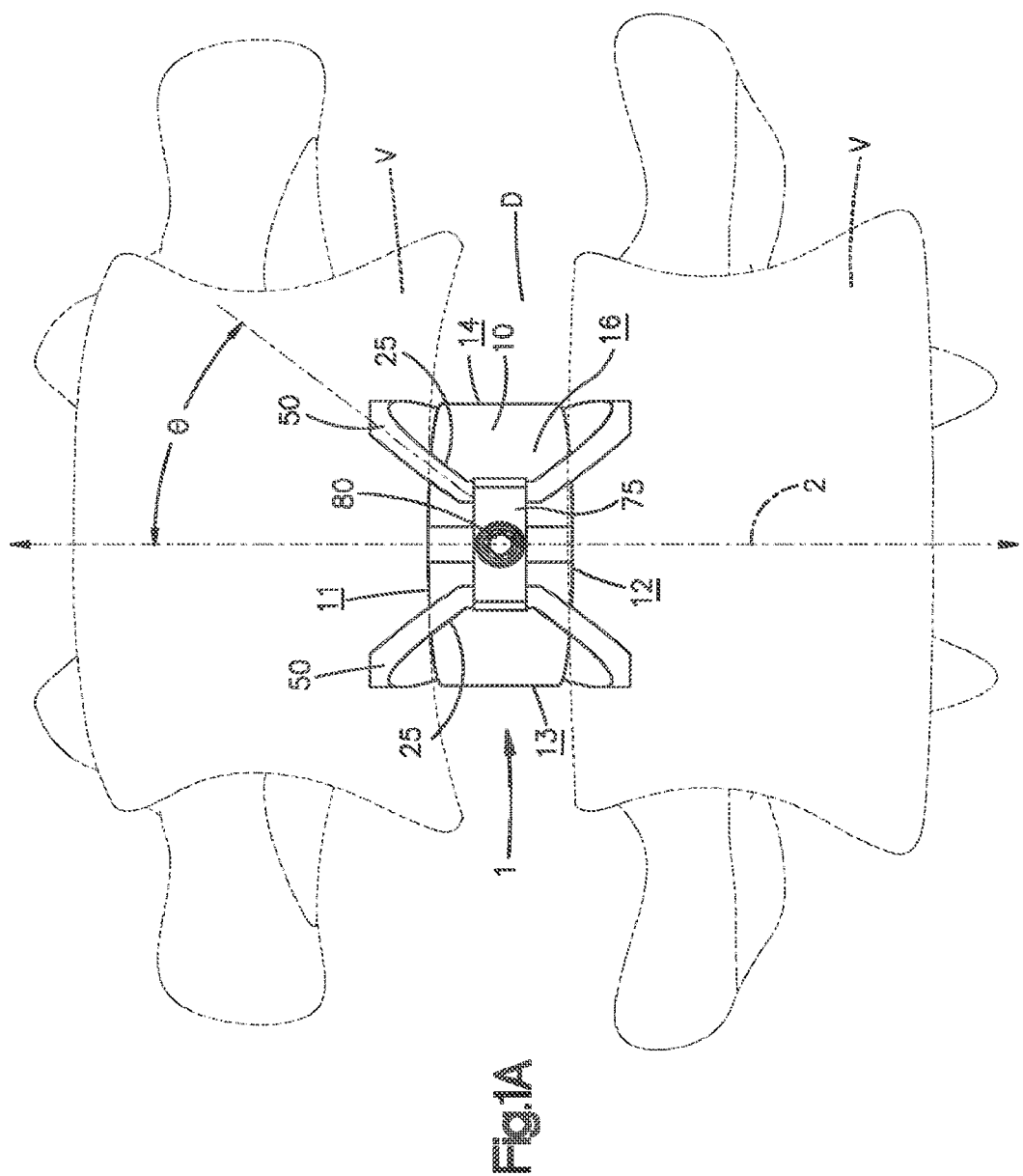
FIG. 1A illustrates an anterior elevational view of an intervertebral implant according to a first preferred embodiment of the present application, the intervertebral implant inserted into an intervertebral disc space between adjacent vertebral bodies.

Certain terminology is used in the following description for convenience only and is not limiting. The words "right", "left", "lower", "upper", "top", and "bottom" designate directions in the drawings to which reference is made. The words "inwardly" or "distally" and "outwardly" or "proximally" refer to directions toward and away from, respectively, the geometric center of the intervertebral implant, spacer, blade elements and related parts thereof. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Similar reference numerals will be utilized throughout the application to describe similar or the same components of each of the preferred embodiments of the intervertebral implant described herein and the descriptions will focus on the specific features of the individual embodiments that distinguish the particular embodiment from the others.

Preferred embodiments of the present application are directed to an implant 1, 100, 200, 300, 400, 400' ("1-400"), preferably an intervertebral implant 1-400. It should be understood that while the various embodiments of the intervertebral implant 1-400 will be described in connection with spinal surgery, those skilled in the art will appreciate that the intervertebral implant 1-400, as well as the components thereof, may be used for implantation into other parts of the body, including, for example, long bones or bones in the hand, face, feet, extremities, cranium or nearly any bone in the human body including the knee, hip, shoulder, finger or other joint replacement or for bone augmentation. For example, the implant 1-400 may be used to fix a fracture of a long bone B (FIGS. 2A-2D), for retaining a graft therein, or in cases where it is desirable to lengthen a long bone B, the implant 1-400 may be inserted into a surgically created fracture between bone portions B1, B2 of the long bone B and then fixed to the bone portions B1, B2. For example, the implant 1-400 may be inserted between the bone portions B1, B2 to fix the bone portions B1, B2 together, such as in the case of a fracture between the bone portions B1, B2.

The various embodiments of the implant 1-400 are preferably sized and configured to be implanted between adjacent vertebral bodies V. The intervertebral implant 1-400 may be sized and configured to replace all or substantially all of an intervertebral disc space D between adjacent vertebral bodies V or only part of the intervertebral disc space D. In addition, the preferred intervertebral implant 1-400 may be configured to replace an entire vertebral body V and related disc spaces D or multiple disc spaces D in a patient's spine, as would be apparent to one having ordinary skill in the art based upon a review of the present application. The intervertebral implant 1-400 may be adapted for use in the anterior, antero-lateral, direct lateral, extra-foraminal, transforaminal, and posterior approaches for insertion into the spine.

The intervertebral implant 1-400 of each of the preferred embodiments preferably includes a spacer portion 10, 110, 210, 310, 410, 410' ("10-410"), preferably an intervertebral spacer portion 10-410, sized and configured for implantation into the intervertebral disc space D between adjacent vertebral bodies V. The spacer portion 10-410 of each of the preferred embodiments includes a top surface 11, a bottom surface 12, a first side surface 13, a second side surface 14, a leading surface 15 and a trailing surface 16. The top and bottom surfaces 11, 12 are suitable for contacting and are adapted for being secured relative to the end plates of adjacent vertebral bodies V. The interbody spacer portion 10-410 is preferably sized and configured to maintain and/or restore a desired intervertebral disc height between the adjacent vertebral bodies V. The trailing surface 16 preferably includes a recess 112 for receipt of a blocking plate 75, as will be described in greatly detail below.

The top and bottom surfaces 11, 12 may include a series of teeth, ridges, spikes or other similar projections 90 to aid in securing the intervertebral implant 1-400 to the endplates of the adjacent vertebral bodies V. Alternatively and/or in addition, the implant 1-400 may include one or more bone fixation elements 442, preferably bone screws 442 (referring to FIGS. 10A-11), and/or the top and bottom surfaces 11, 12 may include one or more keels 92 (referring to FIG. 13) for securing the intervertebral implant 1-400 to the adjacent vertebral bodies V.

The top and bottom surfaces 11, 12 may also include a curved or a tapered surface to help provide an anatomical shape for mating with the patient's spine, to mate with a surface of one of the fractured bone portions B1, B1 or to orient the endplates of the adjacent vertebral bodies V in a desired manner. The particular surface shape and curvature, taper or alternate surface feature in the anterior-posterior direction, as well as the particular surface shape and curvature, taper or alternate surface feature in the medial-lateral direction will depend upon the location where the intervertebral implant 1-400 is intended to be implanted and/or surgeon preferences or whether the implant 1-400 is utilized in a long bone B or other area in the body.

The intervertebral implant 1-400 of the preferred embodiments also includes a longitudinal axis 2 that extends between the top surface 11 and the bottom surface 12 and is preferably, generally parallel to the cranial-caudal axis of the spine. The intervertebral implant 1-400 also includes an anterior-posterior axis 3 that extends generally parallel to the anterior-posterior axis of the spine or generally perpendicular to the aforementioned longitudinal axis 2. The intervertebral implant 1-400 further includes a medial-lateral axis 4 that extends generally parallel to the medial-lateral axis of the spine or generally perpendicular to the aforementioned longitudinal and anterior-posterior axes 2, 3.

The implant 1-400 may also include one or more openings, windows or channels for receiving bone graft material. For example, the implant 1-400 may include one or more vertical openings, windows or channels 96 extending through the implant 1-400 from the top surface 11 to the bottom surface 12 for insertion of bone graft material, such that bone growth is promoted through the vertical openings, windows or channels 96 following implantation of the intervertebral implant 1-400. Alternatively or in addition, the implant 1-400 may include one or more horizontal openings, windows or channels 97 extending through the implant 1-400 from the first side surface 13 to the second side surface 14 and/or from the leading surface 15 to the trailing surface 16 for receiving bone graft material that may also promote fusion through and around the spacer portion 10-410.

The implant 1-400 preferably also includes one or more blade receiving channels 25, 125, 225, 325, 425 ("25-425") configured for mating with the one or more blade elements 50, 150, 250, 350, 450, 450' ("50-450") so that, in use, after the implant 1-400 has been inserted into the intervertebral disc space D between adjacent vertebral bodies V, the implant 1-400 may be secured to the adjacent vertebral bodies V by one or more blade elements 50-450. The blade elements 50-450 preferably limit relative motion between the implant 1-400 and the adjacent vertebral bodies V in an implanted configuration. The intervertebral implant 1-400 is preferably fixedly secured to the adjacent vertebral bodies V, so that, even if the boney structure of the vertebral bodies V is weakened, there is no loosening between the intervertebral implant 1-400 and the vertebral bodies V. The intervertebral implant 1-400 preferably provides an assembly for interbody fusion and for allowing boney fusion to occur while potentially eliminating additional fixation hardware such as pedicle screws and rods or plates.

The intervertebral implant 1-400 may also include the optional blocking plate 75 for reducing the likelihood that the blade elements 50-450 may postoperatively uncouple from the implant 1-400 and migrate from the disc space D. In use, the blocking plate 75 is affixed to the intervertebral implant 1-400 after the blade elements 50-450 have been coupled to the implant 1-400 and adjacent vertebral bodies V. The blocking plate 75 is preferably secured to the implant 1-400 via a fastener 80. The fastener 80 is preferably a screw for threadably engaging the blocking plate 75 to the implant 1-400. The blocking plate 75 preferably covers at least a portion of the blade elements 50-250 to prevent the blade elements 50-250 from backing out. More preferably, the blocking plate 75 is secured to the implant 1-400 and covers at least a portion of the trailing portion of the blade elements 50-250, as will be described in greater detail below. The preferred threaded screw fastener connection between the blocking plate 75 and the implant 1-400 preferably draws the blade elements 50-250 and the implant 1-400 more closely together in order to provide a more rigid construct. Alternatively, as will be appreciated by one of ordinary skill in the art, the blocking plate 75 may be secured using any other coupling mechanism now or hereafter known for such purpose including, but not limited to, a snap-lock, a quarter-turn locking mechanism, a press-fit taper lock, etc. Alternatively, the coupling mechanism may be incorporated into the blocking plate 75 such that the blocking plate 75 secures itself thereto.

The implant 1-400 including the spacer portion 10-410 and the blades 50-250 may be constructed of any suitable biocompatible material or combination of materials including, but not limited to one or more of the following metals such as titanium, titanium alloys, stainless steel, aluminum, aluminum alloy, magnesium, etc., polymers such as, PEEK, porous PEEK, carbon fiber PEEK, resorbable polymers, PLLA, etc., allograft, synthetic allograft substitute, ceramics in the form of bioglass, tantalum, Nitinol, or alternative bone growth material or some composite material or combination of these materials. As will be appreciated by one of ordinary skill in the art, the implant 1-400 may also be coated with various compounds to increase bony on-growth or in-growth, promote healing, or allow for revision of the implant, including hydroxyapatite, titanium-nickel, vapor plasma spray deposition of titanium, or plasma treatment to make the surface hydrophilic.

Referring to FIGS. 1A, 1B and 3A-4, the intervertebral implant 1 of a first preferred embodiment includes the interbody spacer portion 10 and one or more of the blade elements 50. The intervertebral implant 1 is preferably adapted for anterior insertion, but is not so limited and may be otherwise inserted into a disc space.

The interbody spacer portion 10 is constructed as a hollow body, which includes the vertical opening, window or channel 96 extending from the top surface 11 to the bottom surface 12 and has a general kidney-bean shape. Alternatively, as will be appreciated by one of ordinary skill in the art, the interbody spacer portion 10 may assume the structure and geometry of any number of now known or hereafter developed spacer implants.

The interbody spacer portion 10 of the first preferred embodiment includes two blade receiving channels 25 for accommodating a pair of the blade elements 50. In the first preferred embodiment, each of the channels 25 is formed in the trailing surface 16 and extends across the top and bottom surfaces 11, 12 to the leading surface 15 of the implant 1. Alternatively, as will be appreciated by one of ordinary skill in the art, the blade receiving channels 25 may only be formed in the trailing surface 16, may be eliminated entirely so that the blades 50 may be implanted into the adjacent vertebral bodies V and optionally, connected to one another independent of and not mechanically coupled to the interbody spacer portion 10.

Figure 3B:
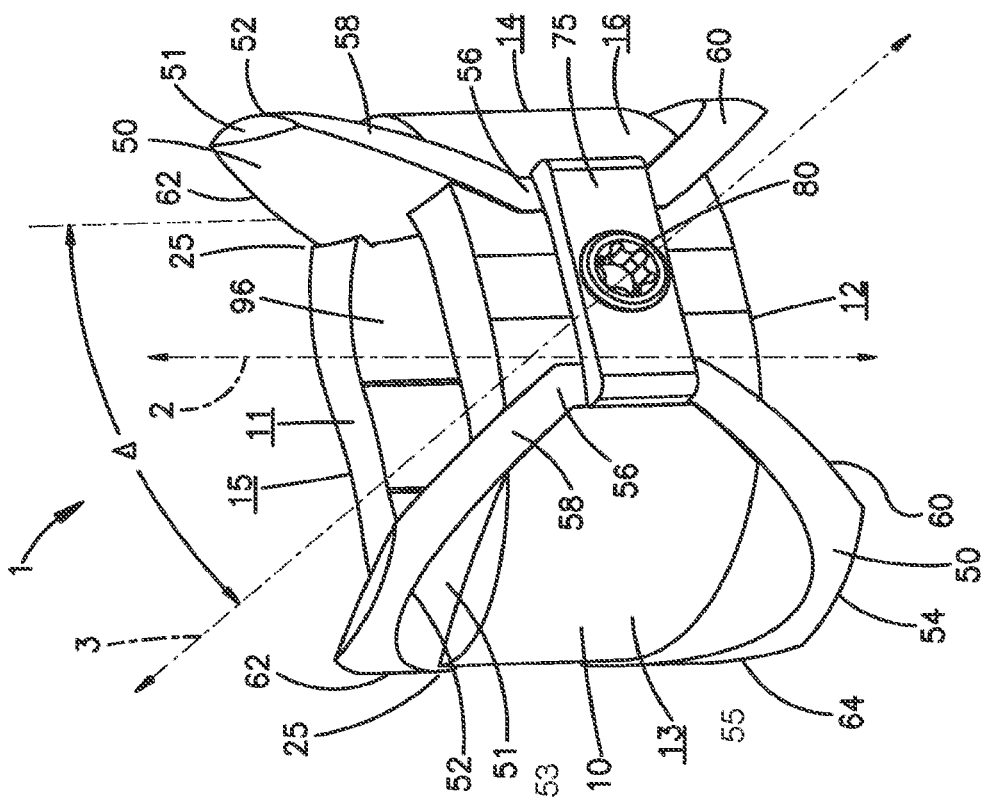
FIG. 3B illustrates an alternate top perspective view of the intervertebral implant shown in FIG. 1A, showing an alternate blocking plate.
Figure 3A:
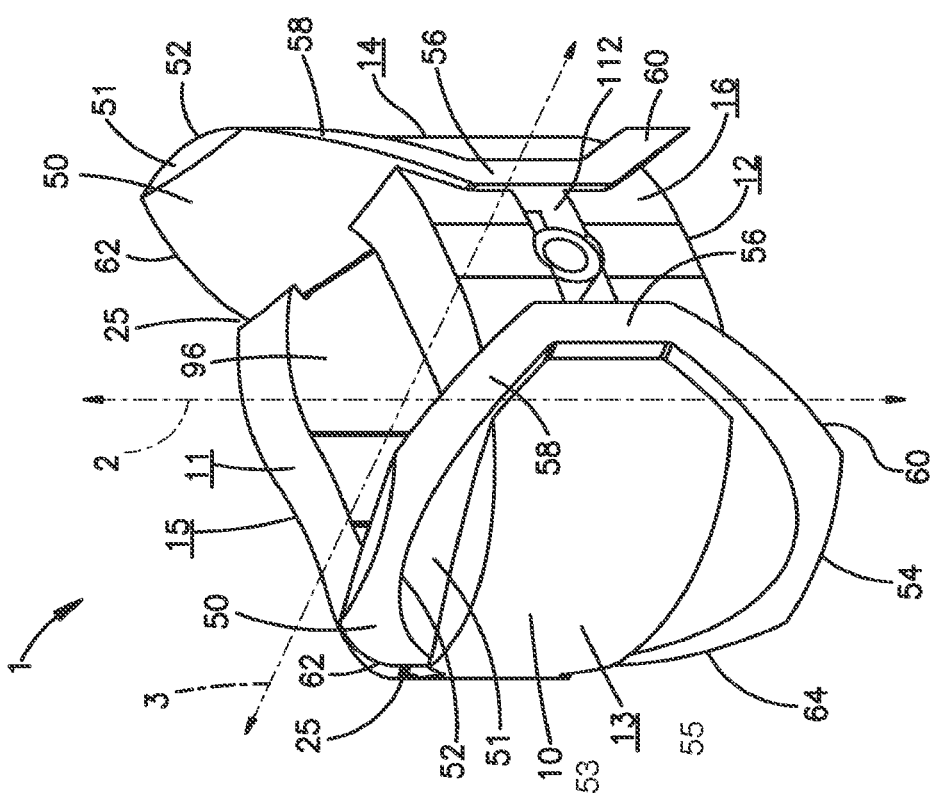
FIG. 3A illustrates a top perspective view of the intervertebral implant shown in FIG. 1A.
Figure 4:
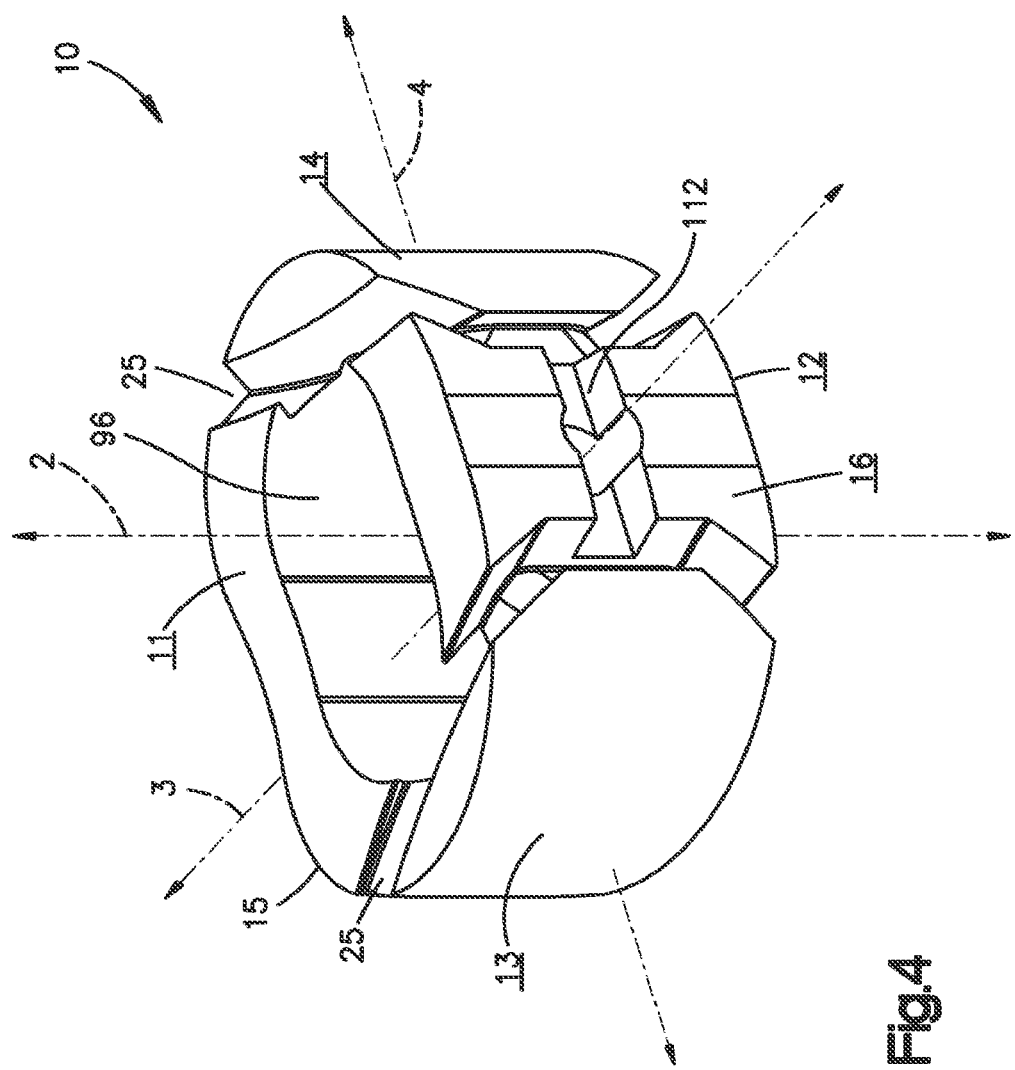
FIG. 4 illustrates a top perspective view of a spacer portion of the intervertebral implant shown in FIG. 1A.

The blades 25 may assume a range of geometries to adapt to user preferences, patient anatomy, various applications, etc. Referring to FIGS. 3A, 3B and 5A, the blades 50 preferably include a superior portion 52, an inferior portion 54, and a trailing portion 56. The superior and inferior portions 52, 54 generally extend in the anterior-posterior direction and extend superiorly and inferiorly of the top and bottom surfaces 11, 12, respectively, of the implant 1 for engaging the adjacent vertebral bodies V while the trailing portion 56 generally extends in the cranio-caudal direction for insertion into the blade receiving channels 25 formed in the trailing surface 16 of the implant 1. The superior portions 52 of the first and second blade elements 50 extend superiorly of the top surface 11 of the spacer portion 10 and the inferior portion 54 of the first and second blade elements 50 extend inferiorly of the bottom surface 12 of the spacer portion 10 in an assembled configuration.

The superior portion 52 is preferably angled obliquely at a first blade angle $\theta$ (FIG. 1) with respect to the longitudinal axis 2. The inferior portion 54 is also preferably angled obliquely at a first blade angle $\theta$ with respect to the longitudinal axis 2. The trailing portions 56 are preferably, generally parallel to the longitudinal axis 2. Alternatively, the superior and inferior portions 52, 54 may extend generally parallel to the anterior-posterior axis 3 from the trailing surface 16 toward the leading surface 15 (generally illustrated in FIGS. 10A-10D), may extend in a generally arcuate path (generally illustrated in FIG. 6) or any combination thereof. In addition, the superior portion 52 of the blades 50 preferably extends from the trailing portion 56 toward the leading surface 15 at a second blade angle $\Delta$ relative to the anterior-posterior axis 3. The inferior portion 54 of the blades 50 may also be similarly oriented relative to the spacer portion 10 and/or the longitudinal and anterior-posterior axes 2, 3. Such orientation of the blades 50 relative to the longitudinal and anterior-posterior axes 2, 3 inhibits backout of the implant 1-400 through the incision through which that implant 1-400 was inserted.

Referring to 1A, 1B, 3A, 3B and 6, the blades 50 preferably are coupled to the implant 1 and the adjacent vertebral bodies V along a pair of divergent and/or curved paths with respect to the longitudinal and anterior-posterior axes 2, 3 from the trailing surface 16 to the leading surface 15. The inclusion of the blades 50 that diverge with respect to the longitudinal and anterior-posterior axes 2, 3 enables the implant 1 to resist translational forces transmitted to the implant 1 when the vertebral bodies V attempt to slide anteriorly. In addition, this geometry preferably forces the adjacent vertebral bodies V into compression about the implant 1 during insertion of the blades 50. The inclusion of the divergent blades 50 with respect to the longitudinal and anterior-posterior axes 2, 3 along a curved path may be particularly well suited for insertion in through a minimal invasive surgical procedure. Alternatively, the blades 50 may diverge along a linearly divergent path.

Preferably, the blade elements 50 are designed to create compression across the implant 1 by creating a difference in the first blade angle $\theta$ of the blades 50 with respect to the longitudinal axis 2 between the leading and trailing ends of the blades 50. That is, for example, the leading end of the superior and inferior portions 52, 54 of the blade elements 50 may have a greater first blade angle $\theta$ than the trailing ends of the superior and inferior portions 52, 54 of the blade elements 50 with respect to the longitudinal axis 2 so that the advancement of the blades 50 into the adjacent vertebral bodies V draws the adjacent vertebral bodies V together about the implant 1. Such a feature may reduce the relaxation of the ligaments which may result in the loosening of the implant 1.

The oblique angles of the superior and inferior portions 52, 54 of the blades 50 can be characterized by defining the blade angle $\theta$ between about ten (10°) and about eighty degrees (80°) with respect to the longitudinal axis 2 and serve to limit anatomical motions of the adjacent vertebral bodies V, such as extension and lateral bending, that tend to separate the vertebral bodies V from the implant 1 and impede fusion.

Referring to FIGS. 3A, 3B and 5A, the blades 50 may further include a superior intermediate trailing portion 58 for interconnecting the superior portion 52 to the trailing portion 56 and an inferior intermediate trailing portion 60 for interconnecting the inferior portion 54 to the trailing portion 56. The superior and inferior intermediate trailing portions 58, 60 may be obliquely angled with respect to the trailing portion 56. The superior and inferior intermediate trailing portions 58, 60 may also be tilted obliquely with respect to the trailing portion 56 in an anterior-posterior direction.

The blades 50 may also include a superior leading portion 62 and an inferior leading portion 64, wherein the superior leading portion 62 may be obliquely angled with respect to the superior portion 52. Similarly, the inferior leading portion 64 may be obliquely angled with respect to the inferior portion 54. The superior and inferior leading portions 62, 64 may also be tilted obliquely with respect to the superior and inferior portions 52, 54.

As best shown in FIG. 5A, inner edges of the superior leading portion 62, the superior portion 52, the superior intermediate trailing portion 58, the trailing portion 56, the inferior intermediate trailing portion 60, the inferior portion 54 and the inferior leading portion 64 preferably define a cavity 65. That is, the trailing portion 56 may terminate prior to the leading edge of the blades 50, thereby defining the cavity 65. The trailing portion 56 may alternatively be eliminated such the blades 50 are mounted to the top and bottom surfaces 11, 12 of the implant 1. The blades 50 preferably have a generally C-shape defined by the superior portion 52, the inferior portion 54 and the trailing or intermediate portion 56 with the cavity 65 defined therein and opening proximate the leading portion 62.

The blades 50 may also include a cutting feature or sharp edge 51 on their leading and/or outer edges such that the blades 50 may be urged or impacted into the adjacent vertebral bodies V or to ease initial insertion of the leading and/or outer edges into a pre-cut channel in the vertebral bodies V. The blades 50 may be urged and/or impacted into the vertebral bodies V without the use of tool cutting instrumentation and while using a relatively minimal surgical incision. Alternatively, a separate tool cutting instrument may be used to form the blade receiving channels in the adjacent vertebral bodies V, as will be described in greater detail below.

Referring to FIG. 5A, the blade elements 50 may be solid. Alternatively, as shown in FIGS. 5B and 5C, the blade elements 50', 50" may include one or more voids 66 therethrough to allow bone-ingrowth to interdigitate with the blade elements 50', 50" imparting additional unity between the implanted blade elements 50', 50" and the boney environment of the vertebral body V. Alternatively or in addition, referring to FIG. 5D, the blade elements 50''' may include anti-repulsion surface features, such as serrations or shark teeth 67, to assist in preventing the blade elements 50''' from backing out of the bone and to allow bone growth between the teeth of the serrations 67.

Alternatively, the blades 50 may assume other geometries now or hereafter developed. For example, the cavity 65 may be eliminated (not shown) such that the blades 50 extend from the inferior portion 54 to the superior portion 52. In such a configuration, the blades 50 may be mounted to the top and bottom surfaces 11, 12. Alternatively, the blades 50 may be configured in a generally X-shape or other similar configuration (not shown) so that the blade elements overlap one another such that a first blade element extends between a superior right side to an inferior left side and a second blade element extends between a superior left side to an inferior right side such that the blade elements form an X when viewed from the trailing surface. Alternatively, the blade elements may be integrally formed in an X-shape (not shown). Further, the orientation of the blades 50, when viewed from the trailing surface along the anterior-posterior axis 3, can be rotated by ninety degrees (90°) such that each blade element interfaces with only a single vertebral body V and couples to the implant 10 or to the other blade element. In addition, the blade elements 50 may be formed from a single component whose flexible construction, for example, a Nitinol construction assists in creating a diverging pattern by way of the blade receiving channels 25 within the interbody spacer portion 10.

The blade elements 50 are preferably integrally formed. Alternatively, the blade elements 50 may be formed from multiple different elements, which are then coupled together by any means now or hereafter developed including but not limited to bonding, a mechanical connection, etc.

In use, the interbody spacer portion 10 is preferably inserted into the desired intervertebral disc space D or void created by the removal of at least a portion of an intervertebral disc. The blade elements 50 may be impacted so that they are received within the blade receiving channels 25 formed in the interbody spacer portion 10. The blade elements 50 may also simultaneously cut or form a channel into the adjacent vertebral bodies V. The blade elements 50 may be impacted so that insertion of the blade elements 50 into the blade receiving channels 25 and the adjacent vertebral bodies V is performed without the use of a tool cutting instrument and with a relatively minimal surgical incision. Alternatively, as will be appreciated by one of ordinary skill in the art, a chisel, broach, saw, drill, milling system, or any other tool cutting instrument may be used to cut a channel through a portion of the adjacent vertebral bodies V prior to implantation of the blade elements 50. For example, referring to FIGS. 14-17, a tool cutting instrument 530 may be guided to cut a channel through a portion of the adjacent vertebral bodies V prior to implantation of the blade elements 50, as will be described in greater detail below. Alternatively, the interbody spacer portion 10 and the blade elements 50 may be coupled together and subsequently inserted together as an assembly into the disc space D, with or without the use of a precut channel in the adjacent vertebral bodies V.

Referring to FIGS. 7A-7D, an intervertebral implant 100 in accordance with a second preferred embodiment is similar to the first preferred embodiment of the implant 10. The intervertebral implant 100 of the second preferred embodiment includes a spacer portion 110 and one or more blade elements 150. In the second preferred embodiment, the blade receiving channels 125 are preferably formed in the trailing surface 16 of the spacer portion 110 from the top surface 11 to the bottom surface 12 only. The blade elements 150 preferably include a superior portion 152, an inferior portion 154, and a trailing portion 156. The superior and inferior portions 152, 154 generally extend in the anterior-posterior direction and are located superiorly and inferiorly of the top and bottom surfaces 11, 12, respectively, of the spacer portion 110 for engaging the adjacent vertebral bodies V while the trailing portion 156 generally extends in the cranio-caudal direction for insertion into the blade receiving channels 125 formed in the trailing surface 16 of the spacer portion 110.

In the second preferred embodiment, the inner edges of the blade elements 150 do not contact the top and bottom surfaces 11, 12 of the spacer portion 110 adjacent to the leading surface 15 of the implant 100. The blades 150 are preferably coupled to the implant 100 and the adjacent vertebral bodies V along a pair of divergent, curved paths, similar to the implant 10 of the first preferred embodiment. Alternatively, the superior and inferior portions 152, 154 of one or more of the blade elements 150 may extend generally parallel from the trailing surface 16 to the leading surface 15 (referring to FIGS. 10A-10D) or any combination thereof.

The blades 150 may also include a cutting feature or sharp edge 151 on their leading surfaces so that the blades 150 can be impacted or otherwise urged into the adjacent vertebral bodies V and into the blade receiving channels 125 formed in the implant 100 without the use of tool cutting instrumentation and while using a relatively minimal surgical incision. Alternatively, a separate tool cutting instrument may be used to form the blade receiving channels in the adjacent vertebral bodies V, as will be described in greater detail below.

The implant 100 may also include a blocking plate 75 and one or more fasteners 80 for securing the blocking plate 75 to the trailing surface 16 of the spacer portion 110. More preferably, the trailing surface 16 of the spacer portion 110 includes a recess 112 for receiving the blocking plate 75. As previously described, in use, after the implant 100 has been inserted into the intervertebral disc space D and the blades 150 have been inserted into the blade receiving channels 125 formed in the spacer portion 110 and into the adjacent vertebral bodies V, the blocking plate 75 can be coupled to the spacer portion 110 via one or more fasteners 80 to prevent the blades 150 from backing out. The blocking plate 75 is preferably received in the recess 112 to limit the protrusion of the blocking plate 75 from the trailing surface 16 and from a profile of the patient's spine. Limiting protrusion of the blocking plate 75 from the profile of the patient's spine generally limits contact between the blocking plate 75 and vessels, nerves or other anatomy adjacent the patient's spine.

Referring to FIGS. 8A and 8B, an intervertebral implant 200 in accordance with a third preferred embodiment includes a spacer portion 210, a plate portion 230 and one or more blade elements 250. The implant 200 is similar to the first and second preferred embodiments of the implant 10, 100 described above. The intervertebral implant 200 of the third preferred embodiment includes a plate portion 230 coupled to the spacer portion 210. The plate portion 230 is preferably mounted to the trailing surface 16 of the spacer portion 210 and preferably does not extend beyond the vertical or lateral perimeter of the interbody spacer portion 210. That is the height of the plate portion 230 is preferably no more than the height of the interbody spacer portion 210 so that the plate portion 230 does not increase the height profile of the interbody spacer portion 210 and the width of the plate portion 230 does not extend beyond a width of the spacer portion 210. In this manner, the intervertebral implant 200 has a low profile. Additionally, in this manner, the plate portion 230 may be entirely implanted into the intervertebral disc space D between the adjacent vertebral bodies V such that the plate portion 230 does not extend beyond an edge of the disc space D. In use, the plate portion 230 may be sized and configured so that the top and bottom surfaces of the plate portion 230 contact the endplates of the adjacent vertebral bodies V. Alternatively, the plate portion 230 may be sized and configured so that only the spacer 210 contacts the adjacent vertebral bodies V. For example, the height of the plate portion 230 may be small enough so that it does not contact the vertebral bodies V when connected to the spacer portion 210 in an implanted position.

The plate portion 230 may be coupled to the interbody spacer portion 210 by any coupling mechanism now or hereafter known. For example, the spacer portion 210 may include one or more recesses 319 (shown in FIG. 9B) formed in the side or trailing surfaces for engaging one or more projections 331 (shown in FIG. 9B) extending from the plate portion 230. Other coupling mechanisms for coupling the plate portion 230 to the spacer portion 210 are disclosed in International Application No. PCT/US2008/082473 filed on Nov. 5, 2008 and entitled, "Low Profile Intervertebral Implant", the contents of which are hereby incorporated by reference in their entirety.

The spacer portion 210 may be constructed of any biocompatible material or combination of materials as previously described. The plate portion 230 may be formed of a different material than the spacer 210. For example, the plate portion 230 may be formed of a metallic material such as, a titanium or a titanium alloy, or a polymer such as, PEEK, and the spacer 210 may be formed of a non-metallic material such as, an allograft, a bioresorbable material, a ceramic, etc. Alternatively, the plate portion 230 and the spacer 210 may be formed from the same material. For example, the plate portion 230 and the spacer 210 may both be constructed of tantalum nitride (TaN).

The plate portion 230 preferably further includes the blade receiving channels 225 for receiving the blade elements 250. The blade elements 250 may have any shape and configuration as disclosed herein. Referring to FIG. 8B, the blades 250 are preferably tapered in the cranial-caudal direction so that when the tapered surfaces are drawn together during the insertion of the blade elements 250 and, optionally, the final tightening of the blocking plate 75, the implant 200 becomes a rigid construct and thus provides an environment for fusion. The tapered geometry of the blade elements 250 further allows a significant portion of the endplates of the adjacent vertebral bodies V to be spared from embedding of the blade elements 250 thus reducing the invasiveness of the surgical procedure. Alternatively, it is envisioned that the blade elements 250 may be integrally formed with the plate portion 230, as will be described in greater detail below.

The implant 200 of the third preferred embodiment may also include a blocking plate 75 and one or more fasteners 80 for securing the blocking plate 75 to the trailing surface of the plate portion 230. More preferably, the trailing surface of the plate portion 230 includes a recess 212 for receiving the blocking plate 75. As previously described, in use, after the implant 200 has been inserted into the intervertebral disc space D and the blades 250 have been inserted into the blade receiving channels 225 formed in the plate portion 230 and into the adjacent vertebral bodies V, the blocking plate 75 can be coupled to the plate portion 230 via one or more fasteners 80 to inhibit the blades 250 from backing out relative to the plate portion 230.

It should be noted, that it is envisioned that the plate portion 230 and the blades 250 may be used without the spacer portion 210 coupled thereto. For example, it is envisioned that the user may insert the spacer portion 210 separately and uncoupled from the plate portion 230. Alternatively, the user may elect to fill the disc space with bone graft material in place of the spacer portion 210 and then insert only the plate portion 230 and the blades 250 or an integrally formed combination of the plate portion 230 and blades 250 (See FIG. 10D).

Referring to FIGS. 9A and 9B, an intervertebral implant 300 in accordance with a fourth preferred embodiment includes an interbody spacer portion 310, a plate portion 330 and a pair of blade elements 350. The plate portion 330 is operatively coupled to the spacer portion 310 as previously described. The plate portion 330 preferably includes a plurality of blade receiving channels 325 for receiving the pair of blade elements 350.

The fourth preferred embodiment of the intervertebral implant 300 is similar to the intervertebral implants 10, 100, 200 of the first through third preferred embodiments. However, in the fourth preferred embodiment the superior and inferior portions 352, 354 of the blade elements 350 are in the form of cylindrical pins 360, in contrast to the generally flatter blade portions, for example, superior and inferior portions 52, 54 of the first preferred embodiment. By incorporating and/or substituting cylindrical pins 360 for the blade elements 350, stress concentration on the vertebral endplates caused by insertion of the cylindrical pins 360 may be generally reduced compared to the relatively flat blades of the first, second and third preferred embodiments. In addition, insertion of the cylindrical pins 360 enables the user to pre-drill boreholes into the adjacent vertebral bodies V for receiving the pins 360. Drilling boreholes typically limits chiseling and/or hammering and chiseling and/or hammering may require exertion of significant force by a surgeon in very dense bone (sclerotic bone).

The blade elements 350 may include a trailing portion 356 for interconnecting the top and bottom cylindrical pins 360 or for connecting the blade elements 350 to the spacer portion 310 or to the plate portion 330. Preferably the cylindrical pins 360 and trailing portion 356 are integrally formed. Alternatively, the cylindrical pins 360 and trailing portion 356 may be separately formed and coupled together by any means now or hereafter developed including but not limited to bonding, mechanical connection, etc. Alternatively, it is envisioned that the blade elements 360 may be integrally formed with the plate portion 330, as will be described in greater detail below.

The cylindrical pins 360 generally extend in the anterior-posterior direction and are located superiorly and inferiorly of the top and bottom surfaces, respectively, of the spacer portion 310 for engaging the adjacent vertebral bodies V while the trailing portion 356 generally extends in the cranio-caudal direction for insertion into the blade receiving channels 325 formed in the trailing surface of the plate portion 330. The blade elements 350 may further include a superior intermediate trailing portion 357 for interconnecting the superior pin 360 to the trailing portion 356 and an inferior intermediate trailing portion 358 for interconnecting the inferior cylindrical pin 360 to the trailing portion 356 so that the superior and inferior cylindrical pins 360 may be angled and/or titled with respect to the trailing portion 356, as previously mentioned.

In use, the spacer portion 310 and the plate portion 330 may be inserted into the desired intervertebral disc space D or void created by the removal of at least a portion of an intervertebral disc. The blade elements 350 are then preferably guided into predrilled boreholes formed in the adjacent vertebral bodies V and impacted, if necessary, into the blade receiving channels 325 formed in the plate portion 330.

The implant 300 may also include a blocking plate 75 and one or more fasteners 80 for securing the blocking plate 75 to the trailing surface of the plate portion 330. More preferably, the trailing surface of the plate portion 330 include a recess 312 for receiving the blocking plate 75. As previously described, in use, after the implant 300 has been inserted into the intervertebral disc space D and the blades 350 have been inserted into the blade receiving channels 325 formed in the plate portion 330 and into the adjacent vertebral bodies V, the blocking plate 75 can be coupled to the plate portion 330 via one or more fasteners 80 to prevent the blades 350 from backing out. In the fourth preferred embodiment, the blades 350 are preferably inserted along a longitudinal axis of the pins 360 and the trailing portions 356 are received into the blade receiving channels 325 that are angled relative to the anterior-posterior axis 3 to accommodate such insertion of the blades 350.

Referring to FIGS. 10A-10C, an intervertebral implant 400 in accordance with a fifth embodiment preferably includes an interbody spacer portion 410. In the fifth preferred embodiment, the intervertebral implant 400 is preferably adapted as a stand alone, laterally insertable implant 400. That is, the implant 400 is sized and configured to be inserted using a direct lateral trans-psoas approach that reduces the need for supplemental rigid fixation such as lateral plates and posterior pedicle screws.

The interbody spacer portion 410 preferably includes a top surface 411, a bottom surface 412, a first side surface 413, a second side surface 414, a leading surface 415 and a trailing surface 416. The leading surface 415 of the implant 400 preferably has a bullet-nosed or tapered geometry to facilitate distraction between the adjacent vertebral bodies V during implant insertion or to generally facilitate initial insertion of the spacer portion 410 into the disc space D. In the fifth preferred embodiment, the first and second side surfaces 413, 414 of implant 400 each have a length that is longer than a distance between the first and second side surfaces 413, 414 or a length of the leading and trailing surfaces 415, 416 so that, upon implantation, the implant 400 has a medial-lateral width that is generally longer than its anterior-posterior depth. The interbody spacer portion 410 is preferably manufactured from a radiolucent polymer, although the spacer portion 410 may be made from other biocompatible materials as outlined above. The top and bottom surfaces 411, 412 of the spacer portion 410 may include a plurality of teeth, ridges, spikes or other topographical features 90 to facilitate fixation of the spacer portion 410 to the adjacent vertebral bodies V.

As previously described above in connection with the third and fourth embodiments, the intervertebral implant 400 of the fifth preferred embodiment includes a plate portion 430 operatively coupled to the trailing surface 416 of the spacer portion 410. The plate portion 430 preferably includes one or more blade receiving channels 425 for receiving one or more blade elements 450 for engaging the adjacent vertebral bodies V. The superior and inferior portions of the blade element 450 are preferably in the form of cylindrical pins 460. More preferably, as shown, the blade element 450 includes a top cylindrical pin 460 for engaging a first vertebral body V, a bottom cylindrical pin 460 for engaging a second vertebral body V and a trailing portion 456 for interconnecting the top and bottom cylindrical pins 460.

The plate portion 430 preferably also includes a threaded hole 461 for threadably engaging an insertion and guide instrument 500, as will be described in greater detail below. The threaded hole 461 preferably is sized and configured to couple a blocking plate 75 via a fastener 80, as previously described, so that when all of the blade elements 450 are inserted into the blade receiving channels 425 formed in the plate portion 430, the blades 450 are preferably fixed to the implant 400 via the blocking plate 75 and fastener 80.

In use, the blade elements 450 are designed to engage the cortical and cancellous bone of the adjacent vertebral bodies V when the implant 400 is positioned within the intervertebral disc space D. The blade elements 450 stabilize the motion segment in bending, shear and rotation before fusion occurs. In this fifth preferred embodiment, each blade elements 450 is preferably inserted at a different angle with respect to a medial plane. Since the blade elements 450 are all inserted at different angles there is no one direction in which the implant 400 will not resist migration. Once the implant 400 and blade elements 450 have been rigidly attached via the blocking plate 75 and fastener 80 to the plate portion 430, the implant 400 will resist movement of the motion segment in bending, shear and rotation. This design will allow the surgeon to stabilize a motion segment to create an environment conducive to interbody fusion, generally without the use of anterior column plating or posterior screw/rod fixation. This allows the surgeon to create a stable interbody fusion construct from a direct lateral approach while containing all of the stabilization hardware within the confines of the anterior column.

As shown, the implant 400 of the fifth preferred embodiment and, specifically, the plate portion 430, may also include one or more bone fixation holes 440 for receiving one or more bone fixation elements or screws 442 for securing the intervertebral implant 400 to the adjacent vertebral bodies V. The bone fixation elements 442 are not limited to bone screws and may be comprised of a helical nail, a distally expanding nail or screw, etc. More preferably, the plate portion 430 includes at least two bone fixation holes 440 for receiving two bone fixation elements 442 with at least one bone fixation element 442 being angled down for engaging the lower vertebral body V and at least one bone fixation element 442 being angled up for engaging the upper vertebral body V. It should be understood however that the number of bone fixation elements 442 extending from the top and bottom surfaces 411, 412 may be varied and that the number of bone fixation elements 442 extending from the top surface 411 need not equal the number of bone fixation elements 442 extending from the bottom surface 412. Exit openings for the bone fixation holes 440 may be formed in the plate portion 430 and/or in the spacer portion 410. The bone fixation holes 440 may also include one or more threads (not shown) for threadably engaging threads formed on a head portion of the bone fixation elements 442 in order to secure the bone fixation elements 442 to the plate portion 430.

It should be noted, that while the blade elements 450 are preferably in the form of cylindrical pins 460 (as shown in FIGS. 10A-10C), referring to FIG. 11, the blade elements 450 may be in the form of flatter blades as previously described and illustrated above. Moreover, referring to FIG. 12, the plate portion 430 may include two or more blade receiving channels 425, wherein each blade 450 includes a trailing portion 456 for receipt within one of the rod receiving channels 425 and a blade portion 452, 454 for engaging one of the adjacent vertebral bodies V. Referring to FIG. 13, the implant 400 of the fifth preferred embodiment may also include one or more keels 92 extending from top and bottom surfaces 411, 412 of the spacer portion 410 instead of the bone fixation elements 442 for engaging the adjacent vertebral bodies V.

Referring to FIG. 10D, the intervertebral implant 400' of the fifth preferred embodiment may include a plate portion 430' for operatively engaging the spacer portion 410' and one or more blade elements 450' for engaging the adjacent vertebral bodies V, wherein the blades 450' are integrally formed with the plate portion 430'. In this manner, the implant 400' may be sequentially inserted such that the spacer 410' may be initially inserted into the intervertebral disc space and the plate portion 430' with integral blades 450' may be sequentially inserted thereafter. Alternatively, the plate portion 430' with integral blades 450' may be initially coupled to the spacer 410' so that the spacer 410', the plate portion 430' and the blades 450' may be inserted simultaneously. The plate portion 430' may be coupled to the spacer 410' by any mechanism now or hereafter known for such purpose including, but not limited to, interlocking projections and recesses, a threaded connection, adhesive, bonding, etc.

Referring to FIGS. 14-17, an exemplary insertion and guide instrument 500 is preferably configured to facilitate insertion of the implant 1-400 including the spacer portion 10-410, plate portion 230, 330, 430 and blade elements 50-450, and the formation of blade receiving channels in the adjacent vertebral bodies V for receiving the blade elements 50-450.

Figure 14:
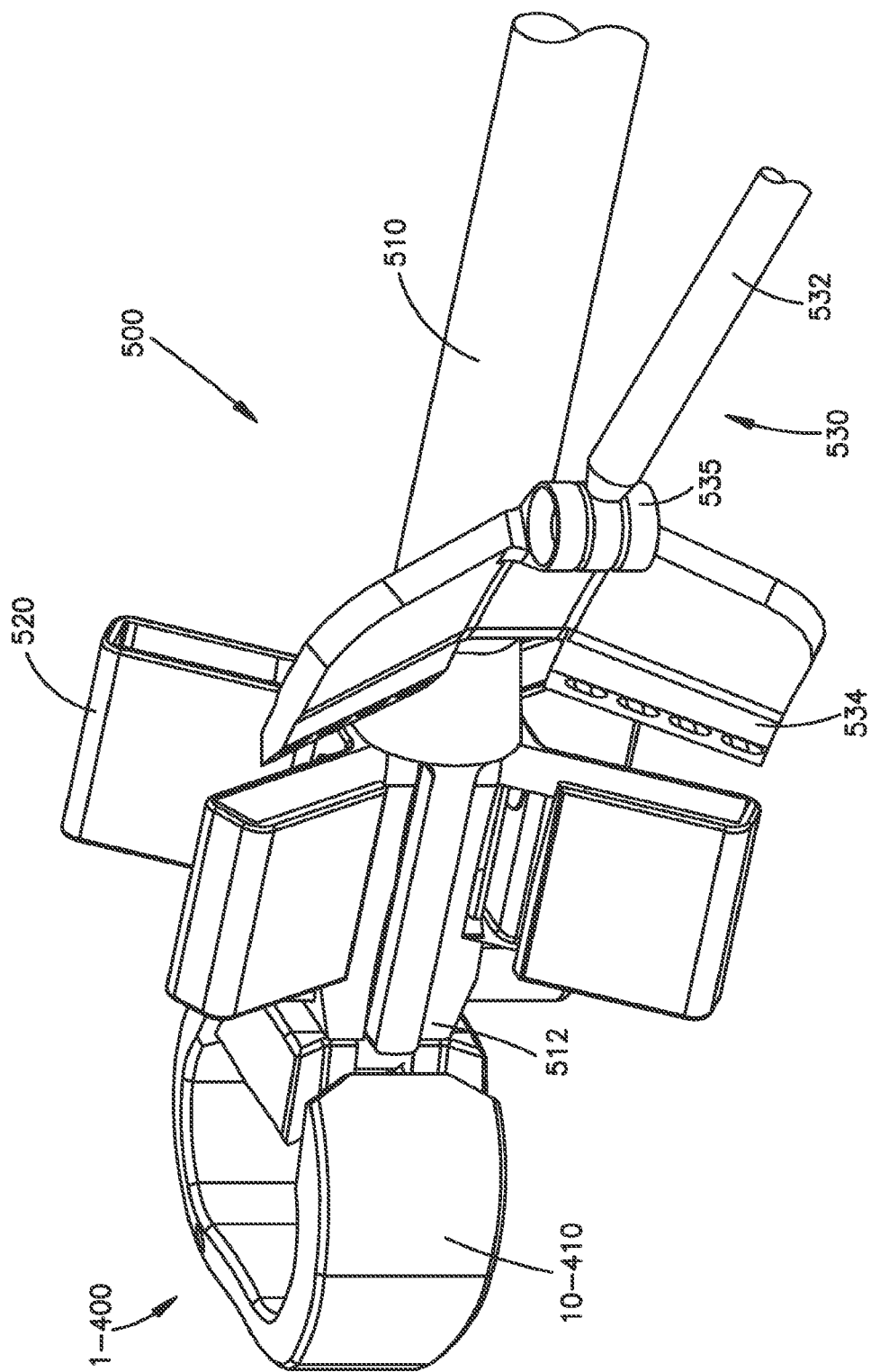

The insertion and guide instrument 500 preferably includes a shaft 510 having a distal end 512 for operatively engaging an intervertebral implant 1-400 to facilitate insertion of the implant 1-400 into the intervertebral disc space D. The shaft 510 may be coupled to the implant 1-400 by any coupling mechanism now or hereafter known for such purpose. For example, the shaft 510 may include a threaded stem (not shown) extending from the distal end 512 for engaging a threaded bore formed in the trailing surface of the implant 1-400. The shaft 512 preferably also includes a stop 515 to prevent over insertion of the implant 1-400 into the disc space D and thus to facilitate optimal positioning of the implant 1-400 with respect to the adjacent vertebral bodies V. The shaft 510 preferably also includes a guide 520 for aligning a cutting tool 530 (FIGS. 14 and 15).

The cutting tool 530 preferably includes a shaft 532 and a cutting tip 534 for forming blade receiving channels in the adjacent vertebral bodies V for receiving the blades 50-450. In use, the cutting tool 530 may be powered such as, for example, via a reciprocating power tool, or hand powered such as, for example, by a mallet or by force applied directly by hand. The cutting tool 530 preferably also includes a pivot 535 such as, for example, a pivot pin or universal ball joint. The pivot 535 allows the cutting tip 534 to be movably disposed with respect to both the shaft 532 of the cutting tool 530 as well as the superior and inferior vertebral bodies V throughout a range of angles.

In use, the insertion and guide instrument 500 is coupled to the implant 1-400. The implant 1-400 is then inserted into a disc space D following, for example, a partial or full discectomy. The insertion and guide instrument 500 is advanced into the disc space D until the stop 515 abuts the adjacent vertebral bodies V. Once the implant 1-400 is positioned within the intervertebral disc space D, the cutting tool 530 is inserted into and through the guide 520 and advanced into the adjacent vertebral bodies V, thereby forming blade receiving channels in the adjacent vertebral bodies V for receiving the blade elements 50-450. Thereafter, the cutting tool 530 is removed and the blade elements 50-450 are advanced through the guide 520 and into the preformed blade receiving channels. The cutting tool 530 is preferably configured to create blade receiving channels that are in a size, shape and/or configuration of the blade element 50-450 that is being utilized with one or the preferred implants 1-400.

Alternatively, the cutting tool 530 may be eliminated and the blade elements 50-450 may be inserted without preformed blade receiving channels formed in the vertebral bodies V. For example, the blade elements 50-450 may be inserted into the adjacent vertebral bodies V by gentle mallet blows to the ends of a blade insertion and guide instrument 500 or any other method of urging the blades 50-450 into the adjacent vertebral bodies V.

Referring to FIGS. 9A-10C, in the fourth and fifth preferred embodiments, where the blade elements 450 incorporate cylindrical pins 460, the guide 520 is preferably sized and configured to guide a drill bit (not shown) in order to form corresponding boreholes in the adjacent vertebra bodies V for receiving the cylindrical pins 360. Thus, in one exemplary method of inserting the intervertebral implants 300, 400 of the fourth and fifth preferred embodiments into the disc space D between first and second vertebral bodies V, the user may insert the implants 300, 400 including, for example, the interbody spacer portion 310, 410 and the plate portion 330, 430 via an insertion and guide instrument 500. Thereafter, using the guide 520 operatively coupled to the insertion and guide instrument 500, the user may drill one or more boreholes in the first vertebral body V and one or more boreholes into the second vertebral body V. Next, the user may guide first and second blade elements 350, 450 into the first and second blade receiving channels 325, 425 formed in the plate portion 330, 430 and into the predrilled first and second boreholes formed in the first and second vertebral bodies V. The predrilled boreholes preferably have a smaller diameter than a diameter of the cylindrical pins 360, 460, resulting in a force-fit between the cylindrical pins 360, 460 and the predrilled boreholes. The user may then couple a blocking plate 75 to the trailing surface of the implant 300, 400 to prevent backing out of the blade elements 350, 450.

It is envisioned that the one or more blade elements 50-450 could be adapted for use in anchoring a disc arthroplasty device (not shown) instead of a fusion spacer 1-400 using similar blade receiving channels 25-425 or by separating the superior and inferior portions of each of the blade element 50-450 and coupling them directly to the endplates of the disc arthroplasty device or dynamic full disc replacement device.

As will be appreciated by those skilled in the art, any or all of the components described herein may be provided in sets or kits so that the surgeon may select various combinations of components to form an implant and create a disc replacement system which is configured specifically for the particular needs/anatomy of a patient. It should be noted that one or more of each component may be provided in a kit or set, including the instruments and tools. In some kits or sets, the same component or part may be provided in different shapes and/or sizes. The surgeon or staff may mix and match the first and second parts to create the implant before or during the procedure.

While the foregoing description and drawings represent the preferred embodiments of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

We claim:

1. An intervertebral implant for insertion into an intervertebral disc space between a firsts vertebral body and a second vertebral body, the implant comprising:
a spacer portion having a top surface for contacting the first vertebral body, a bottom surface opposite the top surface along a downward direction for contacting the second vertebral body, a first side surface, a second side surface, a leading surface, and a trailing surface, the first and second side surfaces each have a length that is longer than a length of each of the leading and trailing surfaces, wherein the top surface of the spacer portion defines an uppermost portion whereby no other portion of the top surface is disposed above the uppermost portion in an upward direction that is opposite the downward direction, and the bottom surface of the spacer portion defines a lowermost portion whereby no other portion of the bottom surface is disposed below the lowermost portion in the downward direction;
a plate portion having a top surface, a bottom surface, a first side surface, a second side surface, a leading surface for operatively contacting the trailing surface of the spacer portion and a trailing surface, the plate portion being coupled to the spacer portion; and
a first cylindrical securement member supported by the plate portion and spaced in its entirety superiorly relative to the uppermost portion of the top surface of the spacer portion, wherein the first cylindrical securement member is configured to be received in the first vertebral body; and
a second cylindrical securement member supported by the plate portion and spaced in its entirety inferiorly relative to the lowermost portion of the bottom surface of the spacer portion, wherein the second cylindrical securement member is configured to be received in the second vertebral body.

2. The intervertebral implant of claim 1, wherein the first and second side surfaces of the spacer portion are opposite each other along a width direction, and the first cylindrical securement member is offset with respect to the second cylindrical securement member along the width direction.

3. The intervertebral implant of claim 1, wherein:
a central plane 1) extends along a first direction that separates the leading surface and the trailing surface and a second direction that extends superiorly and inferiorly, and 2) is positioned equidistantly between the first side surface and the second side surface;
the first cylindrical securement member is disposed on a first side of the central plane; and
the second cylindrical securement member is disposed on a second side of the central plane.

4. The intervertebral implant of claim 1, wherein the first cylindrical securement member comprises a pair of first cylindrical securement members, and the second cylindrical securement member comprises a pair of second cylindrical securement members.

5. The intervertebral implant of claim 4, wherein the first cylindrical securement members of the pair of first cylindrical securement members are spaced in their respective entireties from each other along a direction that separates the first and second side surfaces, the second cylindrical securement members of the pair of second cylindrical securement members are spaced in their respective entireties from each other along the direction that separates the first and second side surfaces of the spacer portion.

6. The intervertebral implant of claim 5, wherein one of the pair of first cylindrical securement members is aligned superiorly with one of the pair of second cylindrical securement members, and another of the pair of first cylindrical securement members is aligned superiorly with another of the pair of second cylindrical securement members.

7. The intervertebral implant of claim 5, wherein the first cylindrical securement members of the pair of first cylindrical securement members are parallel with each other, and the second cylindrical securement members of the pair of second cylindrical securement members are parallel with each other.

8. The intervertebral implant of claim 4, further comprising a blocking plate supported by the plate portion, wherein the blocking plate interferes with the pairs of first and second cylindrical securement members from backing out with respect to the plate portion.

9. The intervertebral implant of claim 8, wherein a screw secures the blocking plate to the plate portion.

10. The intervertebral implant of claim 1, wherein the first and second cylindrical securement members are each adapted to be received in predrilled boreholes in the first and second vertebral bodies.

11. A method for inserting an intervertebral implant into a disc space between a first vertebral body and a second vertebral body, the method comprising the steps of:
coupling the intervertebral implant to an insertion instrument, wherein the intervertebral implant includes a spacer portion having a leading end and a trailing end, and a plate portion coupled to the trailing end;
forming a passageway to the disc space;
inserting the spacer portion into the disc space along an insertion direction defined from the trailing end to the leading end;
inserting a first cylindrical securement member into the first vertebral body, wherein the first cylindrical securement member is supported by the plate portion after the step of inserting the first cylindrical securement member has been completed; and
inserting a second cylindrical securement member into the second vertebral body, wherein the second cylindrical securement member is supported by the plate portion after the step of inserting the second cylindrical securement member has been completed,
wherein an entirety of the first cylindrical securement member is spaced superiorly from a superior-most portion of the spacer portion, and an entirety of the second cylindrical securement member is spaced inferiorly from an inferior-most portion of the spacer portion, and
wherein no portion of the spacer portion is disposed superior of the superior-most portion of the spacer portion, and no portion of the spacer portion is disposed inferior of the inferior-most portion of the spacer portion.

12. The method of claim 11, wherein:
the spacer portion defines first and second side surfaces that extend from the leading end to the trailing end,
a central plane 1) extends along the insertion direction and a second direction that extends superiorly, and 2) is positioned equidistantly between the first side surface and the second side surface;
the first cylindrical securement member is disposed on a first side of the central plane; and
the second cylindrical securement member is disposed on a second side of the central plane.

13. The method of claim 11, wherein:
the first cylindrical securement member comprises a pair of first cylindrical securement members;
the second cylindrical securement member comprises a pair of second cylindrical securement members;
the second inserting step comprises inserting the pair of first cylindrical securement members into the first vertebral body; and
the third inserting step comprises inserting the pair of second cylindrical securement members into the second vertebral body.

14. The method of claim 11, wherein the first cylindrical securement members of the pair of first cylindrical securement members are parallel with each other, and the second cylindrical securement members of the pair of second cylindrical securement members are parallel with each other.

15. The method of claim 11, further comprising the step of blocking backout of each of the first and second cylindrical securement members with a blocking plate that is supported by the plate portion.

16. The method of claim 11, further comprising the step of predrilling first and second holes in the first and second vertebral bodies, respectively, and the second and third inserting steps comprise inserting the first and second cylindrical securement members into the first and second holes, respectively.

* * * * *